(12) United States Patent
Beyar et al.

(10) Patent No.: US 10,194,835 B2
(45) Date of Patent: Feb. 5, 2019

(54) METHOD OF MONITORING VOLUMETRIC CHANGE OF A LUNG

(71) Applicants: MEDICAL RESEARCH INFRASTRUCTURE AND HEALTH SERVICES FUND OF THE TEL AVIV MEDICAL CENTER, Tel Aviv (IL); RESMETRIX MEDICAL LTD., Matam, Haifa (IL)

(72) Inventors: Mordechay Beyar, Caesaria (IL); Oren Globerman, Kfar Shmaryahu (IL); Zvi Reznic, Tel-Aviv (IL)

(73) Assignees: MEDICAL RESEARCH INFRASTRUCTURE AND HEALTH SERVICES FUND OF THE TEL AVIV MEDICAL CENTER, Tel Aviv (IL); RESMETRIX MEDICAL LTD., Haifa (IL)

(*) Notice: Subject to any disclaimer, the term of this patent is extended or adjusted under 35 U.S.C. 154(b) by 274 days.

(21) Appl. No.: 15/078,172

(22) Filed: Mar. 23, 2016

(65) Prior Publication Data
US 2016/0287140 A1    Oct. 6, 2016

Related U.S. Application Data

(60) Provisional application No. 62/141,338, filed on Apr. 1, 2015.

(51) Int. Cl.
| A61B 5/05 | (2006.01) |
| A61B 5/091 | (2006.01) |
| A61B 5/00 | (2006.01) |
| A61B 5/113 | (2006.01) |

(52) U.S. Cl.
CPC ............. *A61B 5/091* (2013.01); *A61B 5/05* (2013.01); *A61B 5/1135* (2013.01); *A61B 5/6823* (2013.01); *A61B 5/6831* (2013.01)

(58) Field of Classification Search
CPC ..... A61B 5/091; A61B 5/6823; A61B 5/1135; A61B 5/6831; A61B 5/05
USPC ................. 600/301, 425, 500, 534
See application file for complete search history.

(56) References Cited

U.S. PATENT DOCUMENTS

| 3,831,586 | A | 8/1974 | Petit |
| 4,258,718 | A | 3/1981 | Goldman |
| 7,041,062 | B2 * | 5/2006 | Friedrichs ............... A61B 5/08 |
| | | | 600/529 |

(Continued)

*Primary Examiner* — Sanjay Cattungal
(74) *Attorney, Agent, or Firm* — Browdy and Neimark, P.L.L.C.

(57) ABSTRACT

There is provided a method, apparatus, computer program product and wearable device for monitoring volumetric change of a lung during a breathing cycle by using an electronic signal. The method comprises: receiving by a receiver an electronic signal transmitted from a transmitter, wherein at least part of a path of the signal contours at least part of a chest wall of the lung; determining by the receiver measurements of an attribute of the signal received at the beginning and the end of a time interval during the breathing cycle; calculating by a processor a change in length of the signal path during the time interval based on the measurements of the attribute of the signal received at the beginning and the end of the time interval; and calculating by the processor a volumetric change during the time interval based on the change in signal path length.

43 Claims, 8 Drawing Sheets

(56) References Cited

U.S. PATENT DOCUMENTS

| | | | |
|---|---|---|---|
| 7,903,020 B2 | 3/2011 | Lin et al. | |
| 8,790,273 B2 * | 7/2014 | McCool | A61B 5/1135 |
| | | | 324/207.15 |
| 8,971,936 B2 * | 3/2015 | Derchak | A61B 5/0002 |
| | | | 455/500 |
| 2010/0249632 A1 | 9/2010 | Lee et al. | |
| 2011/0060215 A1 * | 3/2011 | Tupin, Jr. | A61B 5/0507 |
| | | | 600/425 |
| 2012/0041279 A1 * | 2/2012 | Freeman | A61B 5/0205 |
| | | | 600/301 |
| 2013/0324875 A1 | 12/2013 | Mestha et al. | |
| 2013/0324876 A1 | 12/2013 | Bernal et al. | |
| 2017/0172519 A1 * | 6/2017 | Stergiou | A61B 5/7278 |

* cited by examiner

METHOD OF MONITORING VOLUMETRIC CHANGE OF A LUNG

CROSS REFERENCE TO RELATED APPLICATIONS

This application claims the benefit of U.S. Provisional Application No. 62/141,338, filed Apr. 1, 2015, which is hereby incorporated by reference herein.

TECHNICAL FIELD

The presently disclosed subject matter relates, in general, to the field of respiratory monitoring, and more specifically, to methods and apparatuses for monitoring volumetric change of a lung during breathing.

BACKGROUND OF THE INVENTION

Respiratory monitoring is critical for patients especially those with severe medical conditions which in turn affect the lung and overall pulmonary functions. Respiratory data, such as tidal volume of the lung, can provide valuable information concerning the progression of a disease or injury affecting a patient, which is very useful for assessing, diagnosing and treating respiratory symptoms driven by such disease or injury. For instance, it is proven that postoperative respiratory volume monitoring can help predict the risk of life-threatening complications in post-surgical patients, which may happen hours after the patients are considered stabilized after the operation. Urgent medical resuscitation is essential in such cases to prevent respiratory failure and death.

Nevertheless, respiratory monitoring could also be important for individuals to use during normal daily routines so as to be able to capture respiratory events which may be indicative of a patient's state of respiratory health and reveal adverse conditions which might otherwise go unnoticed. The breathing of babies at risk for Sudden Infant Death Syndrome (SIDS) is difficult to monitor, and accurate non-invasive monitoring at home may be life saving. Obstructive sleep apnea in adults and children requires accurate respiratory monitoring in order to diagnose and treat. Again, accurate non-invasive respiratory monitoring can facilitate this.

Existing monitoring systems and methods are normally complex, inconvenient, and expensive to be effectively and widely used by patients or individuals. For instance, monitoring a patient's respiratory status usually takes place in a hospital setting or a doctor's office, and the patient is normally observed by being connected to cumbersome medical equipment which prevents the patient from freely moving around. Thus it would be highly desirable to be able to easily and accurately measure respiratory parameters in a manner that allows usages in essentially any location.

Such problems have been recognized in the conventional art and various techniques have been developed to provide solutions. For example:

U.S. patent application Ser. No. 13/486,637 (Bernal et al.) entitled "Processing a video for respiration rate estimation" discloses a system and method for estimating a respiration rate by analyzing distortions in reflections of structured illumination patterns captured in a video containing a view of a subject's thoracic region. In one embodiment, a video of a target region of a body of a subject of interest is received. Video image frames are processed to estimate 3D time-series data for the target region. As more fully disclosed herein, the subject's respiration rate is estimated from the 3D time-series data. Measurements can be acquired under a diverse set of lighting conditions. The teachings hereof provide a non-contact approach to patient respiratory function monitoring that is useful for intensive care units and for monitoring at homes, and which aid in the detection of sudden deterioration of physiological conditions due to changes in respiration rates. The teachings hereof provide an effective tool for non-contact respiratory function study and analysis.

U.S. patent application Ser. No. 12/749,861 (Tupin, J R. et al.) entitled "Apparatus and method for continuous non-invasive measurement of respiratory function and events" discloses an apparatus and method for non-invasive and continuous measurement of respiratory chamber volume and associated parameters including respiratory rate, respiratory rhythm, tidal volume, dielectric variability and respiratory congestion. In particular, a non-invasive apparatus and method for determining dynamic and structural physiologic data from a living subject including a change in the spatial configuration of a respiratory chamber, a lung or a lobe of a lung to determine overall respiratory health comprising an ultra wide-band radar system having at least one transmitting and receiving antenna for applying ultra wide-band radio signals to a target area of the subject's anatomy wherein the receiving antenna collects and transmits signal returns from the target area.

U.S. patent application Ser. No. 13/210,360 (Freeman et al.) entitled "Devices and methods for respiratory variation monitoring by measurement of respiratory volumes, motion and variability" discloses devices and methods for assessing a patient. The devices have at least one impedance measuring element functionally connected to a programmable element, programmed to analyze an impedance measurement, and to provide an assessment of at least one respiratory parameter of the patient. Preferably the device includes electronics which aid in calibration, signal acquisition, conditioning, and filtering.

GENERAL DESCRIPTION

In accordance with certain aspects of the presently disclosed subject matter, there is provided a method of monitoring volumetric change of a lung during a breathing cycle by using an electronic signal, the method comprising: receiving by a receiver an electronic signal transmitted from a transmitter, wherein at least part of a path of the signal contours at least part of a chest wall of the lung; determining by the receiver measurements of an attribute of the signal received at the beginning and the end of a time interval during the breathing cycle; calculating by a processor a change in length of the signal path during the time interval based on the measurements of the attribute of the signal received at the beginning and the end of the time interval; and calculating by the processor a volumetric change during the time interval based on the change in signal path length.

In accordance with other aspects of the presently disclosed subject matter, there is provided an apparatus capable of monitoring a volumetric change of a lung during a breathing cycle by using an electronic signal, the apparatus comprising at least one transmitter and a receiving module, the receiving module including at least one receiver operatively connected to a processor, wherein: the at least one transmitter is configured to transmit the electronic signal, wherein at least part of a path of the signal contours at least part of a chest wall of the lung; the at least one receiver is configured to: receive the electronic signal transmitted from the at least one transmitter, and determine measurements of an attribute of the signal received at the beginning and the end of a time interval during the breathing cycle; the processor is configured to: calculate a change in length of the signal path during the time interval based on the measurements of the attribute of the signal received at the beginning and the end of the time interval; and calculate the volumetric change of the lung during the time interval based on the change in signal path length.

In accordance with other aspects of the presently disclosed subject matter, there is provided a non-transitory computer usable medium having a computer readable program code embodied therein, said computer readable program code adapted to be executed to perform a method of monitoring volumetric change of a lung during a breathing cycle by using an electronic signal, including: receiving by a receiver an electronic signal transmitted from a transmitter, wherein at least part of a path of the signal contours at least part of a chest wall of the lung; determining by the receiver measurements of an attribute of the signal received at the beginning and the end of a time interval during the breathing cycle; calculating by a processor a change in length of signal path during the time interval based on the measurements of the attribute of the signal received at the beginning and the end of the time interval; and calculating by the processor a volumetric change during the time interval based on the change in signal path length.

In accordance with other aspects of the presently disclosed subject matter, there is provided a wearable device integrating an apparatus capable of monitoring a volumetric change of a lung during a breathing cycle by using an electronic signal, the apparatus comprising at least one transmitter and a receiving module, the receiving module including at least one receiver operatively connected to a processor, wherein: the at least one transmitter is configured to transmit the electronic signal, wherein at least part of a path of the signal contours at least part of a chest wall of the lung; the at least one receiver is configured to: receive the electronic signal transmitted from the at least one transmitter, and determine measurements of an attribute of the signal received at the beginning and the end of a time interval during the breathing cycle; the processor is configured to: calculate a change in length of the signal path during the time interval based on the measurements of the attribute of the signal received at the beginning and the end of the time interval; and calculate the volumetric change of the lung during the time interval based on the change in signal path length.

In accordance with other aspects of the presently disclosed subject matter, there is provided a wearable device operating in accordance with a method of monitoring volumetric change of a lung during a breathing cycle by using an electronic signal, the method comprising: receiving by a receiver an electronic signal transmitted from a transmitter, wherein at least part of a path of the signal contours at least part of a chest wall of the lung; determining by the receiver measurements of an attribute of the signal received at the beginning and the end of a time interval during the breathing cycle; calculating by a processor a change in length of the signal path during the time interval based on the measurements of the attribute of the signal received at the beginning and the end of the time interval; and calculating by the processor a volumetric change during the time interval based on the change in signal path length.

In accordance with other aspects of the presently disclosed subject matter and optionally, in combination with any of the above aspects, the presently disclosed subject matter may comprise one or more of features (i) to (xx) listed below, in any desired combination or permutation which is technically possible:

(i) the signal is a radio frequency (RF) signal.
(ii) the signal is a single carrier RF signal characterized by a carrier wavelength.
(iii) the single carrier signal is selected such that the carrier wavelength is greater than twice the change in signal path length during the time interval.
(iv) the attribute is phase of the signal.
(v) the signal flows from the transmitter to the receiver through a belt or a strap or a band attached to the chest wall of the lung.
(vi) the change in signal path length is in a linear correlation relationship with a difference between said measurements.
(vii) the attribute is amplitude of the signal.
(viii) the signal is characterized by a predetermined set of frequencies, and the amplitude is an amplitude of each frequency in the set of frequencies relative to amplitudes of other frequencies in the frequency set.
(ix) the determining measurements, calculating a change in signal path length, and calculating a volumetric change are performed for a plurality of time intervals.
(x) the signal is an Ultra-wide Band (UWB) RF signal characterized by a bandwidth larger than 500 Mhz.
(xi) the attribute is time-of-arrival of the signal.
(xii) at least one transmitter and at least one receiver are positioned on the circumference of the chest wall.
(xiii) the time interval is a fraction of the breathing cycle.
(xiv) at least one receiver is connected to a corresponding transmitter by a reference cable that carries a reference signal, a corresponding attribute of the reference signal being indicative of an attribute of a transmitted signal.
(xv) a tidal volume is calculated for the breathing cycle.
(xvi) a respiratory rate is measured and an alarm is generated if the tidal volume is within a pre-specified range, and the respiratory rate is normal.
(xvii) a first indication is generated if the tidal volume is below a first threshold, and a second indication is generated if the tidal volume is above a second threshold, wherein the second threshold is larger than the first threshold and a difference between the first and second threshold is below 10% of normal tidal volume.
(xviii) the processor is a part of the receiver.
(xix) the determining measurements, calculating a change in signal path length, and calculating a volumetric change are performed for a plurality of time intervals, and a breathing pattern is detected from a plurality of pre-defined breathing patterns, based on the volumetric changes during the plurality of time intervals.
(xx) the apparatus comprises a plurality of pairs of transmitters and receivers, the pairs operating with the signal by time division multiple access (TDMA) to avoid signal interference.

BRIEF DESCRIPTION OF THE DRAWINGS

In order to understand the presently disclosed subject matter and to see how it may be carried out in practice, the subject matter will now be described, by way of non-limiting example only, with reference to the accompanying drawings, in which:

FIG. 10A depicts the frequency response when the length of the strap is minimized, and FIG. 10B depicts the frequency response when the length of the strap is maximized in accordance with certain embodiments of the presently disclosed subject matter.

DETAILED DESCRIPTION

Figure 1:
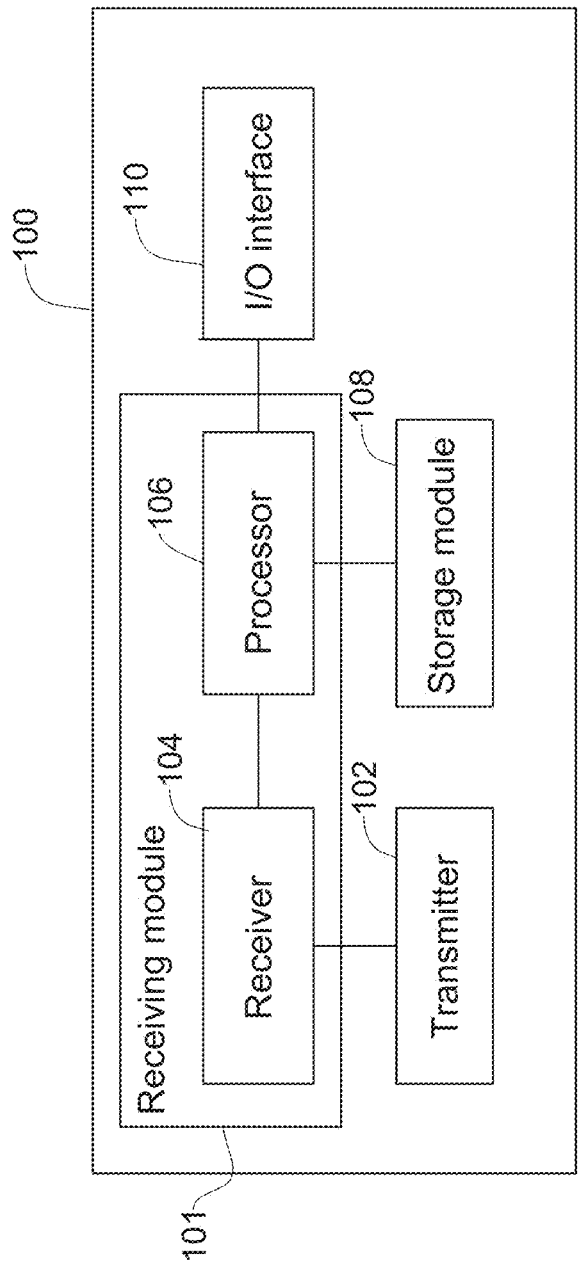
FIG. 1 is a functional block diagram schematically illustrating an apparatus for monitoring volumetric change of a lung during a breathing cycle by using a radio frequency (RF) signal in accordance with certain embodiments of the presently disclosed subject matter.

In the following detailed description, numerous specific details are set forth in order to provide a thorough understanding of the disclosed subject matter. However, it will be understood by those skilled in the art that the present disclosed subject matter can be practiced without these specific details. In other instances, well-known methods, procedures, and components have not been described in detail so as not to obscure the present disclosed subject matter.

In the drawings and descriptions set forth, identical reference numerals indicate those components that are common to different embodiments or configurations.

Unless specifically stated otherwise, as apparent from the following discussions, it is appreciated that throughout the specification discussions utilizing terms such as "receiving", "measuring", "determining", "calculating", "estimating", "transmitting", "monitoring", or the like, may include action and/or processes of a computer that manipulate and/or transform data into other data, said data represented as physical quantities, e.g. such as electronic quantities, and/or said data representing the physical objects. The term "computer" should be expansively construed to cover any kind of electronic device with data processing capabilities, including, by way of non-limiting examples, the apparatus and/or the processor disclosed in the present application.

The operations in accordance with the teachings herein can be performed by a computer specially constructed for the desired purposes or by a general purpose computer specially configured for the desired purpose by a computer program stored in a non-transitory computer readable storage medium.

The term "non-transitory" is used herein to exclude transitory, propagating signals, but to otherwise include any volatile or non-volatile computer memory technology suitable to the presently disclosed subject matter.

It is appreciated that, unless specifically stated otherwise, certain features of the presently disclosed subject matter, which are described in the context of separate embodiments, can also be provided in combination in a single embodiment. Conversely, various features of the presently disclosed subject matter, which are described in the context of a single embodiment, can also be provided separately or in any suitable sub-combination.

Bearing this in mind, attention is drawn to FIG. 1, schematically illustrating a functional block diagram of an apparatus for monitoring volumetric change of a lung during a breathing cycle by using an electronic signal in accordance with certain embodiments of the presently disclosed subject matter. For simplicity's sake, the subject matter is described herein with reference to an RF signal where the range of frequencies can be between 3 Khz to 300 Ghz, but any electronic signal can be used additionally or alternatively, mutatis mutandis.

For example, another electronic signal that can be used can have a frequency, say, of 250 Hz, such as a square wave where the signal changes value, say from +5 Volts to 0 Volts or vice versa every 2 msec.

For simplicity's sake, the subject matter is described with reference to a human patient, but in some cases a patient can alternatively be an animal.

The apparatus 100 illustrated in FIG. 1 comprises at least one transmitter 102 and a receiving module 101. The receiving module includes at least one receiver 104 and a processor 106 that is operatively connected to the at least one receiver 104. The transmitter 102 and/or the receiver 104 can be attached externally to a portion of the chest wall of a lung, and/or can be located anywhere else which enables calculation of a volumetric change of the lung during a breathing cycle. The terms "chest wall" and "chest" are used interchangeably herein. During the breathing cycle, the chest wall moves as the volume of the lung changes. The single form of "lung" used herein should be construed to mean a single lung or a plurality of lungs (e.g. two lungs), as appropriate, and therefore the term volume of the lung can refer to the volume of one lung (e.g. if only one lung is working) or can refer to the sum of the volumes of the plurality of lungs (e.g. if two lungs are working). The at least one transmitter 102 can be configured to transmit the RF signal. The at least one receiver 104 can be configured to receive the transmitted RF signal from the at least one transmitter 102. At least part of the path of the signal contours at least part of the chest wall. This means that at least part of the signal path is on or beside at least part of the chest wall so that the at least part of the signal path adjusts when the at least part of the chest wall moves.

The receiver 104 is further configured to determine measurements of an attribute of the RF signal received by the receiver 104 at two time points, e.g., at the beginning and the end of a time interval during the breathing cycle. According to certain embodiments, the receiver 104 is further configured to determine measurements of an attribute of a received RF signal, for a plurality of time intervals during one or more breathing cycles, e.g. where the determination can be performed periodically or repeatedly. A measurement of an attribute can be determined by the receiver 104, by actively measuring the attribute and/or by accessing a measurement from a previous measuring (e.g. the receiver 104 can measure the attribute at the beginning of a certain time interval and/or can access a measurement made at the end of the previous time interval measurement, say, from the storage module 108, and use this measurement as the measurement for the beginning of the certain time interval if the beginning of the certain time interval is the same time point as at the end of the previous time interval). The functional structure of the transmitter 102 and the receiver 104 of the RF signal will be described in detail with reference to FIG. 3.

Figure 6:
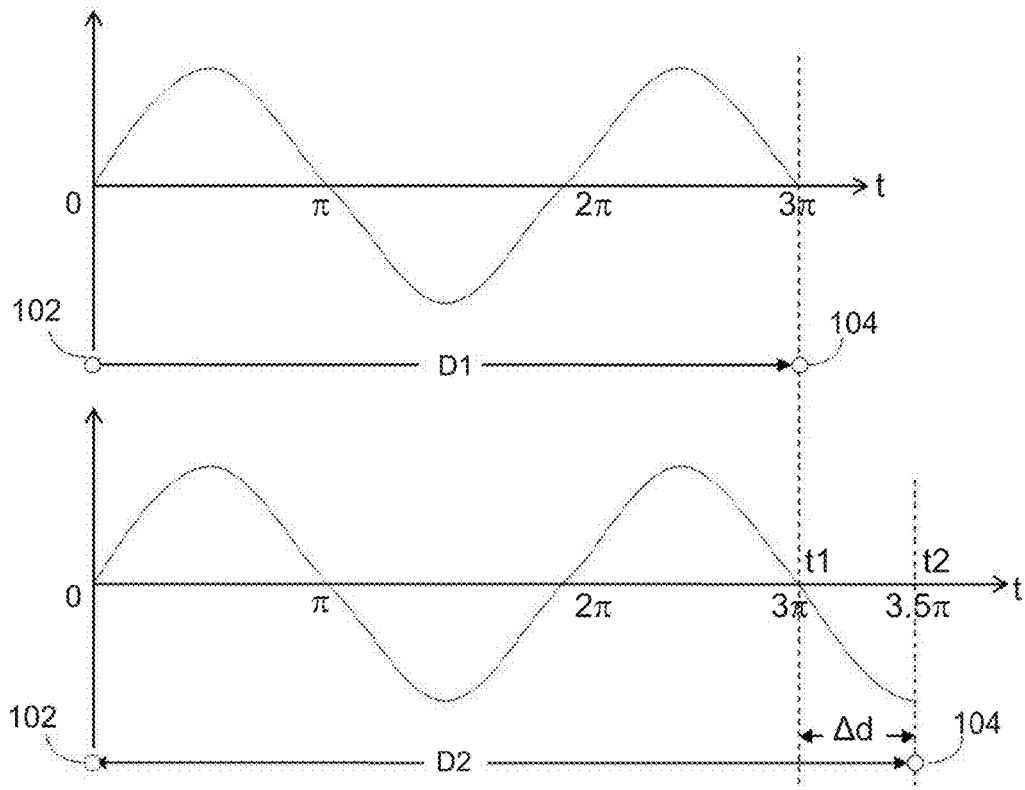
FIG. 6 is an exemplified single carrier signal in a sine waveform utilized in the transmitter and the receiver in accordance with certain embodiments of the presently disclosed subject matter.
Figure 7:
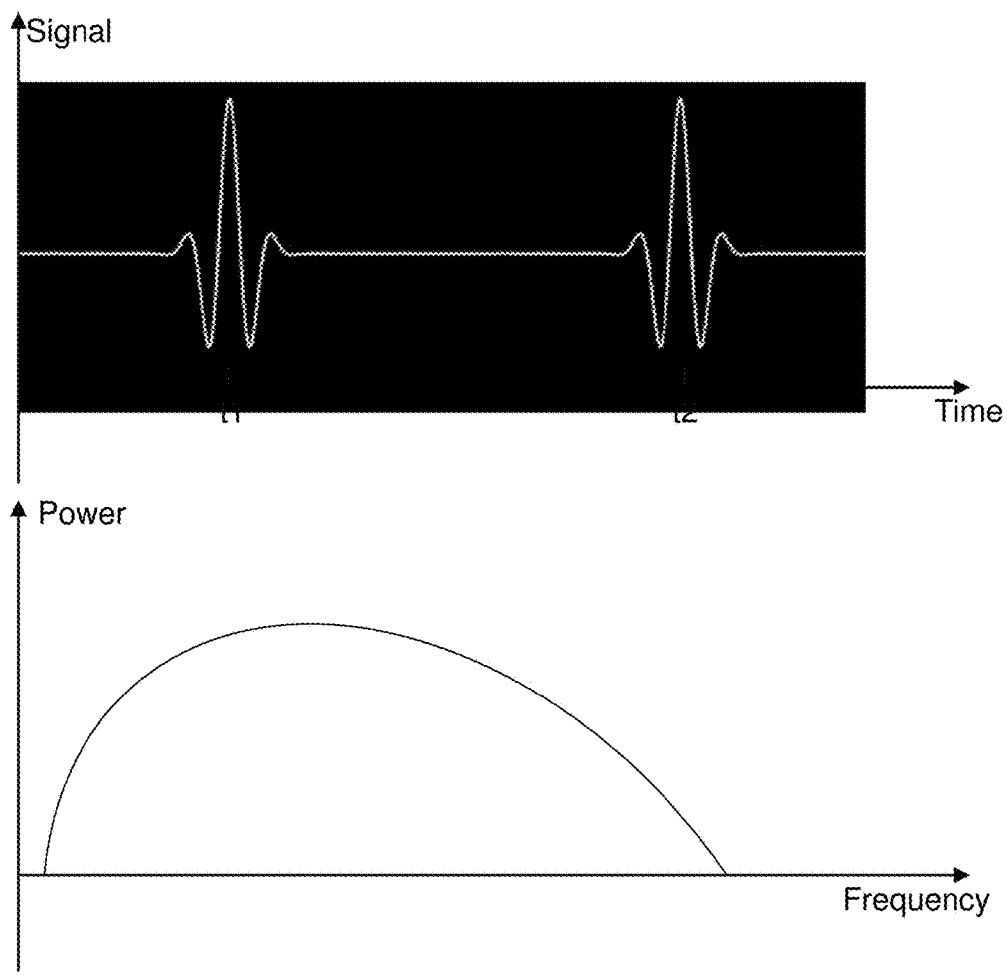
FIG. 7 is a schematic illustration of a Ultra-Wide Band (UWB) signal in time domain and frequency domain in accordance with certain embodiments of the presently disclosed subject matter.

According to certain embodiments, the RF signal can be a single carrier signal characterized by a predetermined wavelength or a predetermined frequency. By way of example, the single carrier signal can be in a sinusoidal carrier waveform with a single frequency, as illustrated in FIG. 6. According to other embodiments, the RF signal can be an Ultra-wide Band (UWB) signal as illustrated in FIG. 7. The UWB signal can be characterized by a wide bandwidth exceeding 500 MHz, and the frequency range can extend from 3.1 GHz to 10.6 GHz. According to other embodiments, the RF signal can be a wideband signal characterized by a bandwidth of 0.1 Mhz to 200 Mhz, and the frequency range can extend from 100 Mhz to 10 Ghz, as discussed with reference to FIG. 10.

The processor 106 can be operatively connected to the receiver 104, and can be configured to calculate a change in the signal path length during the time interval. Specifically, according to certain embodiments, the processor can be configured to calculate a change in the signal path during the time interval based on the measurements of the attribute of the RF signal received at the beginning and end of the time interval. The processor 106 is further configured to calculate the volumetric change of the lung during the time interval based on the change in the signal path length. As at least part of the signal path contours at least part of the chest wall, the signal path length changes when the at least part of the chest wall moves. The chest wall moves as the volume of the lung changes. The processor 106 can therefore calculate the volumetric change of the lung during the time interval based on the change in the signal path length. According to certain embodiments, the processor can be configured to calculate a change in the signal path length and calculate the volumetric change of the lung based on the change in the signal path length, for a plurality of time intervals during one or more breathing cycles, e.g. where the calculation can be performed periodically or repeatedly.

As illustrated in FIG. 1, the apparatus 100 can further comprise a storage module 108 and an I/O interface 110 that are operatively coupled to the processor 106. The storage module 108 comprises a non-transitory computer readable storage medium. According to certain embodiments, the storage module can be configured to store calculation instructions, inputs and outputs related to the processor. The I/O interface 110 can be configured to provide a user with an output of the calculation result, e.g., an illustration of the calculated volumetric change during the time interval, on a monitor. By way of example, the output of the calculated volumetric change can be illustrated in a volumetric-time axis. The I/O interface 110 can be configured to additionally or alternatively provide a user with an output based on the calculation result. For instance, an alarm can be generated if a tidal volume is within a pre-specified range, and a measured respiratory rate is normal. The respiratory rate can be measured in any known manner that measures the number of breaths per minute such as counting the number of times the chest rises per minute. By way of example, the normal respiratory rate for an adult at rest is 12 to 20 breaths per minute. For another instance, a first indication can be generated if a tidal volume is below a first threshold, and a second indication can be generated if the tidal volume is above a second threshold. The second threshold can be larger than the first threshold and the difference between the first and second thresholds can be below 10% of the normal tidal volume. By way of example, the normal tidal volume is approximately 500 mL per inspiration or 7 mL/kg of body mass. For another instance, a breathing pattern can be detected from a set of pre-defined breathing patterns based on volumetric changes during a plurality of time intervals, and indicated to the user (e.g. by way of an alarm). The I/O interface 110 can be configured to additionally or alternatively obtain monitoring instructions from the user. For instance, the user may predetermine the time interval for the apparatus to measure the change of the RF signal attribute, etc. The time interval can be determined, for example, to be a fraction of the breathing cycle.

It should be noted that functions of the processor 106, and/or the I/O interface 110 and/or the storage module 108, can be implemented in a stand-alone manner, which can be used in conjunction with the transmitter(s) 102 and the receiver(s) 104, or alternatively their functions can, at least partly, be integrated with, for example, one or more receiver(s) 104. For example, the processor 106 can be implemented as a part of a given receiver 104, or alternatively, the processor 106 and the given receiver 104 can be implemented as two separate units that are operatively connected with each other.

According to one embodiment, the apparatus can comprise one transmitter and one receiver. According to another embodiment, the apparatus can comprise multiple transmitters and one receiver, or alternatively, one transmitter and multiple receivers. According to yet another embodiment, the apparatus can comprise multiple pairs of transmitter and receiver. In any of these compositions, a transmitter that transmits a signal that is received by a particular receiver can be considered to be a corresponding transmitter for that particular receiver. For purpose of illustration only, parts of the following description are provided with respect to one transmitter and one receiver. Embodiments are, likewise, applicable to any of the above mentioned compositions.

The operation of the apparatus 100 and of the various components thereof is further detailed with reference to FIG. 5.

Figure 5:
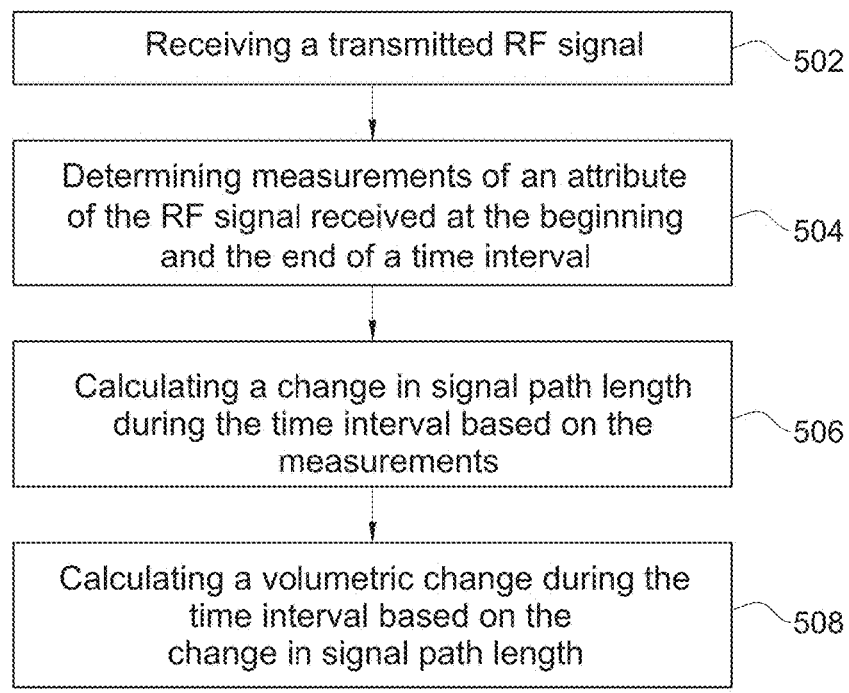
FIG. 5 is a generalized flowchart of monitoring a volumetric change of a lung during a breathing cycle by using RF signal, in accordance with certain embodiments of the presently disclosed subject matter.

While not necessarily so, the process of operation of the apparatus 100 can correspond to some or all of the stages of the method described with respect to FIG. 5. Likewise, the method described with respect to FIG. 5 and its possible implementations can be implemented by the apparatus 100. It is therefore noted that embodiments discussed in relation to the method described with respect to FIG. 5 can also be implemented, mutatis mutandis as various embodiments of the apparatus 100, and vice versa.

Those versed in the art will readily appreciate that the teachings of the presently disclosed subject matter are not bound by the apparatus illustrated in FIG. 1, equivalent and/or modified functionality can be consolidated or divided in another manner and can be implemented in any appropriate combination of software, firmware and hardware.

As mentioned above, at least part of a path of the signal contours at least part of the chest wall. The subject matter does not limit which at least part of the chest wall is contoured. However for the sake of further illustration to the reader, some examples are now presented.

Figure 2A:
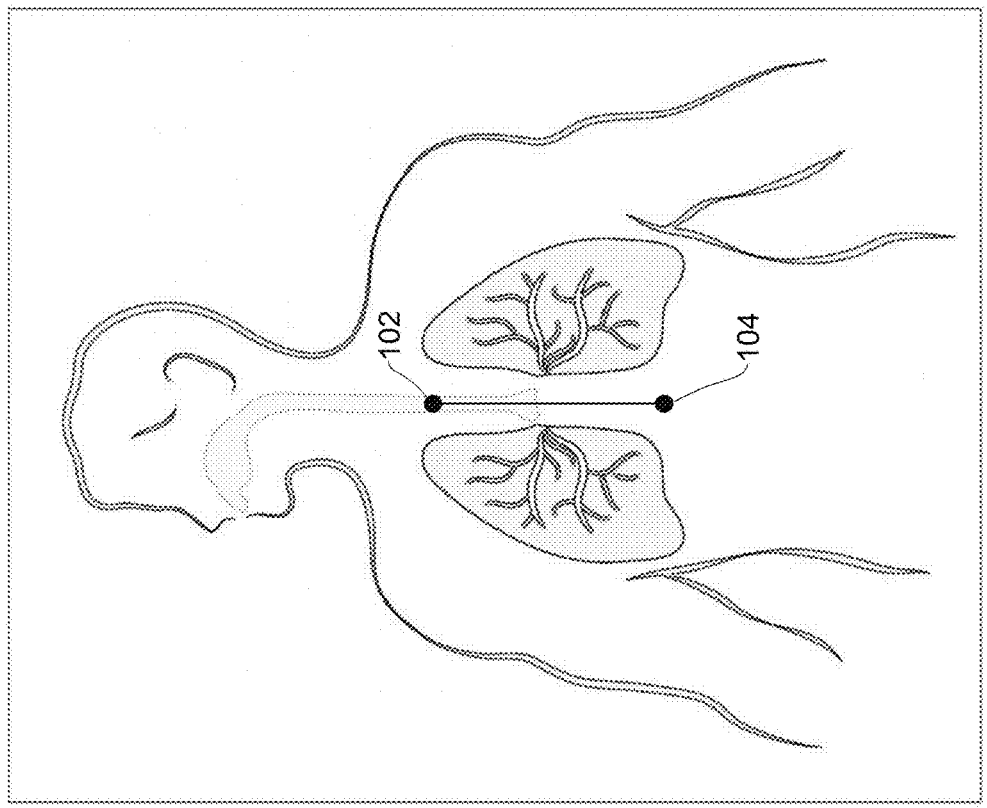
FIGS. 2A and 2B illustrate exemplified placements of one transmitter and one receiver attached to an individual's chest wall in accordance with certain embodiments of the presently disclosed subject matter.
Figure 2B:
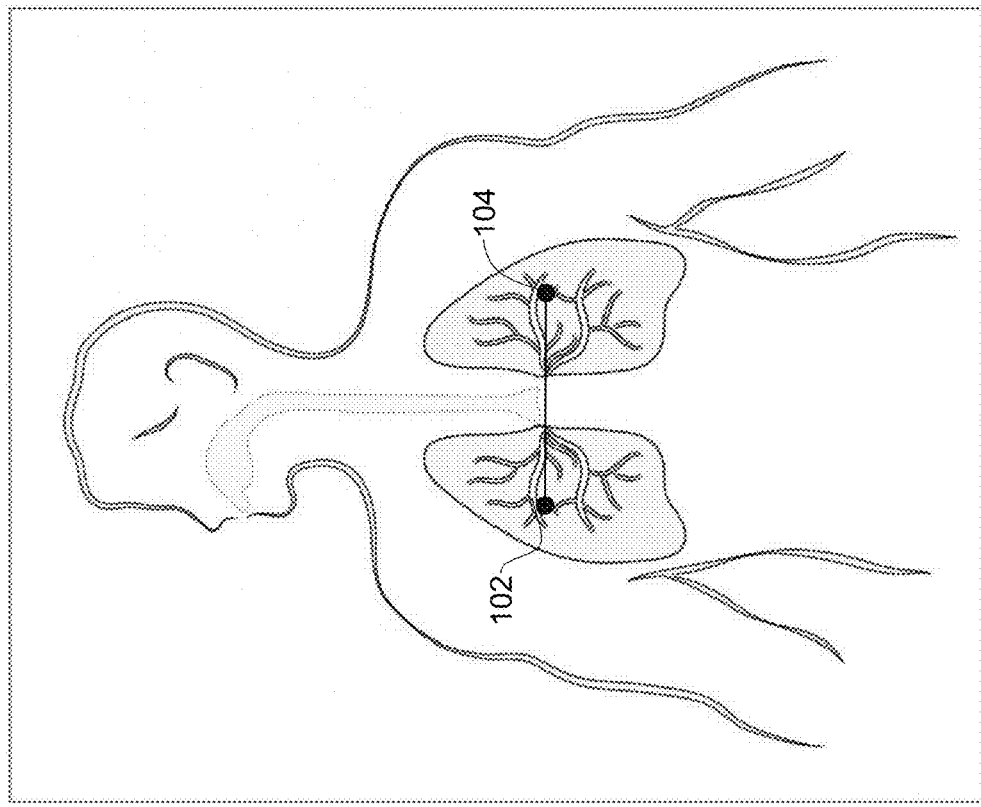

FIGS. 2A and 2B illustrate exemplified placements of a transmitter—102 (or at least an antenna of the transmitter) and a receiver—104 (or at least an antenna of the receiver) attached to an individual's chest wall in accordance with certain embodiments of the presently disclosed subject matter. In accordance with certain embodiments, the signal is transmitted wirelessly between antennas, and therefore can travel through the air between antennas. A signal that travels through the air between antennas can be considered to be a non-guided signal. However, even when the signal travels through the air between antennas, optionally part of the signal path may not be through the air, e.g. if the signal travels from the transmitter to its associated antenna that is located apart, and/or travels from an antenna associated with the receiver to the receiver that is located apart.

According to certain embodiments, the shape of the lung can be assumed to be a ball. The transmitter 102 (or at least the antenna thereof) and the receiver (or at least the antenna thereof) can be placed on the chest wall of the lung. By way of example, the transmitter 102 (or at least the antenna thereof) and the receiver 104 (or at least the antenna thereof) can be positioned horizontally apart in parallel with ribs, as shown in FIG. 2A. By way of another example, the transmitter 102 (or at least the antenna thereof) and the receiver 104 (or at least the antenna thereof) can be positioned vertically apart along the direction of the airway, as shown in FIG. 2B. It is to be noted that the placements in FIGS. 2A and 2B are illustrated for exemplified purposes only, and should not be construed to limit the scope of the present disclosure in any way. Accordingly, the transmitter 102 and receiver 104 (or at least respective antennas) can be positioned in any other suitable places, such as each under an armpit or side of the chest, or alternatively, one attached on the front of the chest, and the other attached on the back of the chest. In cases where there are multiple pairs of transmitter and receiver, the pairs can be positioned in any suitable places, such as one or more pairs of transmitter 102 and receiver 104 (or at least respective antennas) positioned horizontally apart and/or one or more pairs of transmitter 102 and receiver 104 (or at least respective antennas) positioned vertically apart, in any suitable places. Similarly, other compositions of transmitter(s) and receiver(s) can be positioned in any suitable places.

In accordance with certain embodiments, a transmitter 102 and a receiver 104 (or at least the respective antennas) can be placed such that there is a line of sight between the antennas. As the signal is not guided once it leaves the antenna associated with the transmitter 102, the transmitted signal can go in multiple directions, with one of the directions being the line of sight direction, such that at least part of the signal path contours at least part of the chest wall. Possibly there may also be reflected signal(s), due to reflection(s) of the transmitted signal, whose signal path(s) did not contour any part of the chest wall, but which can also be received by the receiving antenna. The signal received directly (line of sight) is significantly larger than reflected signal(s). Therefore, the line of sight signal is dominant in the received signal, and a measurement of an attribute of the received signal (even if including reflected signal(s)), may be considered to be substantially equivalent to a measurement of an attribute of the direct (line of sight) signal. Moreover, since the line of sight signal is dominant, at least part of the path of the signal that is received can be said to contour at least part of the chest wall, because at least part of the path of the line of sight signal contours at least part of the chest wall, regardless of whether or not the signal that is received included reflected signal(s) whose path(s) do not contour any part of the chest wall.

In accordance with certain embodiments, the transmitter 102 (or at least the antenna thereof) and the receiver 104 (or at least the antenna thereof) can be attached to the chest wall with standard adhesives (e.g., adhesive sticker) or to a stretchable garment worn on the torso. Depending on the embodiment, the rest of the transmitter 102 may or may not be located at the same location as the antenna of the transmitter 102 (e.g. may or may not be attached with the same adhesive) and/or the rest of the receiver 104 may or may not be located at the same location as the antenna of the receiver 104 (e.g. may or may not be attached with the same adhesive). In embodiments where the antennas are attached to the chest wall, so that at least part of the signal path contours at least part of the chest wall, but the rest of the transmitter 102 and/or rest of receiver 104 are not attached to the chest wall, the part of the signal path between the transmitter 102 and the respective antenna thereof, and/or between the receiver 104 and the respective antenna thereof may not necessarily contour any part of the chest wall.

Figure 8:
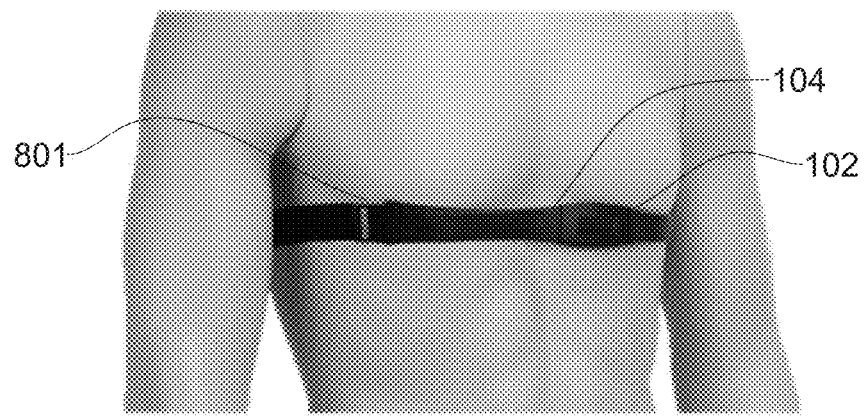
FIG. 8 is an illustration of an example of a strap through which a signal can flow in accordance with certain embodiments of the presently disclosed subject matter.
Figure 9:
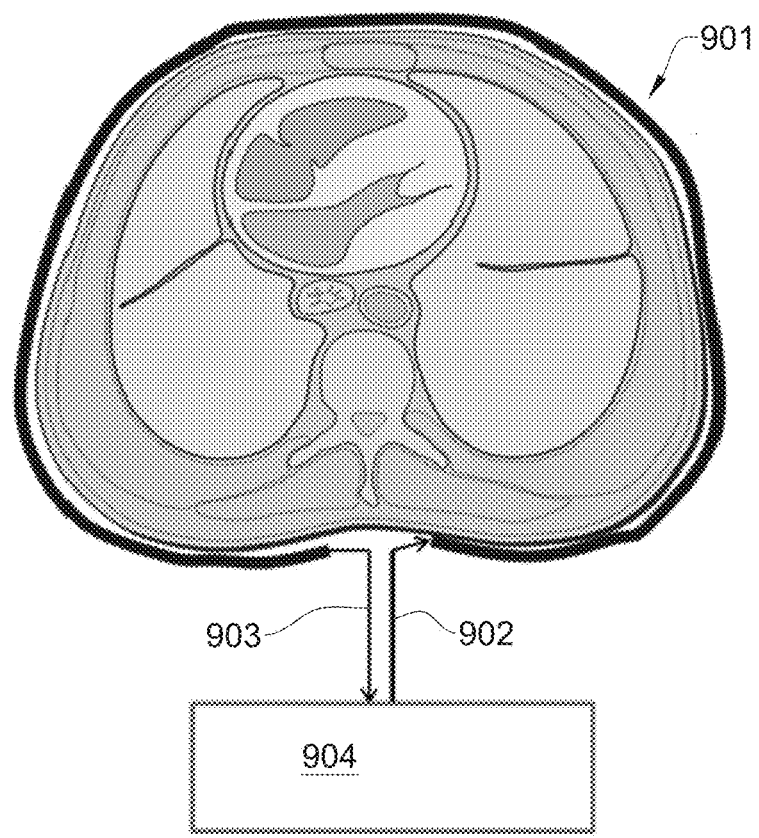
FIG. 9 is an illustration of an example of a strap through which a signal can flow in accordance with certain embodiments of the presently disclosed subject matter.

Refer now to FIGS. 8 and 9 which illustrate certain embodiments where the signal may be guided. For example, the signal can flow for at least part of the path between the transmitter 102 and the receiver 104 through a belt, or a strap or a band, or similar, attached to a chest wall of the lung, so that the path of the signal through at least part of the strap contours at least part of the chest wall. The terms belt, chest strap, strap, band and similar should be construed as equivalent terms for an item through which a signal can travel.

FIG. 8 illustrates a strap 801 through which a signal can flow, in accordance with certain embodiments of the presently disclosed subject matter. In FIG. 8, the strap 801 encircles the chest wall and there is a small central unit (e.g. plastic case) near the chest (e.g. attached to the chest) which includes the transmitter 102 and the receiver 104. The transmitter generates an electronic signal which is transmitted through the strap 801 to the receiver.

FIG. 9 illustrates another example of a strap 901 through which a signal can flow, in accordance with certain embodiments of the presently disclosed subject matter. In FIG. 9, the strap 901 encircles the chest wall. The central unit 904 includes the transmitter 102 and the receiver 104. The transmitter 102 in the central unit 904 generates an electronic signal 902 which is transmitted through a strap 901 to the receiver. The signal 903 exiting the strap 901 enters into the receiver 104 which is inside the central unit 904. The receiver 104 can determine measurements for one or more attribute(s) of the received signal 903. Optionally, attribute(s) of the received signal 903 can also be compared to attribute(s) of the transmitted signal 902.

The signal 902 travels along a wire (or similar connection) before reaching the strap 901 and the signal 903 travels along a wire (or similar connection) after exiting the strap 901. These wires (or similar connections) connecting the strap 901 to the central unit 904 can be of any length. For instance, shorter wires (e.g. 1 cm length) can be used for a smaller central unit 904 (e.g. of size of approximately 4 cm) that can e.g. be attached to the chest. Longer wires (e.g. 3 meters length) can be used for a larger central unit 904 (e.g. size of 40 cm) that can e.g. be set on a table. Therefore, if there is space in the central unit 904, transmitter 102 and receiver 104 may not necessarily be close to one another (e.g. can be up to 30 cm apart, or more, in a unit of 40 cm).

Although straps 801 and 901 are illustrated as encircling the entire chest wall, in certain embodiments, there may not be a total encirclement of the chest wall by a strap. For instance, a strap can be attached to less than 100% (e.g. at least 70%) of the chest wall. In another instance, there can be more than one chest strap (e.g. one attached to the front of the chest wall and one to the back of the chest wall, e.g. one attached horizontally and one attached vertically, etc). In embodiments with a plurality of straps, a separate transmitter 102 and receiver 104 can be located on the two ends of any given strap, two or more straps can share transmitter(s) 102 and/or receiver(s) 104, or one or more straps can have separate transmitter(s) 102 and/or receiver(s) 104 while two or more other straps can share transmitter(s) 102 and/or receiver(s) 104.

Optionally, a strap used in the subject matter can consist of at least three sections. The first section can be operatively connected to a transmitter 102 and to a second section. The second section can be operatively connected between the first section and a third section. The third section can be operatively connected between the second section and a receiver 104. Optionally, the second section can be designed with an impedance that is significantly different than the impedance of the first section and also significantly different than the impedance of the third section. In this case, a standing wave may be created inside the strap, as a result of the impedance mismatch between the different sections of the strap.

It is to be noted that in embodiments with a strap, the signal received by the receiver 104 is typically, although not necessarily, made up solely of the signal that traveled through the strap. In other words, the signal received by the receiver 104 typically although not necessarily does not include any reflected signals whose path(s) did not contour any part of the chest wall, as may be the case when the signal is non-guided due to having been wirelessly transmitted. As mentioned above, the path of the signal through at least part of the strap contours at least part of the chest wall, and therefore at least part of the path of the signal that is received contours at least part of the chest wall.

The subject matter does not limit the makeup of a strap nor which dielectric material is included in a strap. However, for the sake of further illustration some examples are now given. For example, a possible strap can include a polyester elastic ribbon, integrated with two or more curly copper wires with polyurethane coating, such as a conductive elastic ribbon-OHM-e-12-L-1 available from Ohmatex. In this example, the dielectric material includes polyester. For another example, a possible strap can include a stretchable Printed Circuit Board (PCB) where the substrate is made of polyurethane and the conductors are made of copper, the conductors having a curly pattern that allows the conductors to stretch, such as stretch-rigid PCB developed by Q.P I. Group. In this example, the dielectric material includes polyurethane. For another example, a possible strap can be a flexible metal-fabric-rubber waveguide where the dielectric material is rubber and the rubber is coated with a flexible metal-fabric sheet, which reflects the signal which travels through the rubber, such that a flexible waveguide is formed. For another example, a possible strap can be a flexible metal-fabric waveguide where the dielectric material is air.

It is to be noted that determining a measurement of an attribute of an unguided or guided signal that travels through the air or another known dielectric material can be advantageous compared to determining a measurement of an attribute of a signal that travels via dielectric material of a (human) body. Consider that the dielectric material through which a signal travels can affect an attribute of the signal. The dielectric constant of air or of a known dielectric material can be calculated. Furthermore, in the case of a strap, the dielectric constant of the dielectric material in the strap can typically, although not necessarily, be controlled. Therefore, the effect of air or other known dielectric material on the attribute can consequently be taken into account when determining a measurement. Moreover, the dielectric constant of air or of a known dielectric material can be typically, although not necessarily, be expected to remain relatively constant during the monitoring of a patient. Therefore the effect of air or other known dielectric material on an attribute of the received signal can be expected to remain relatively constant or can at least be taken into account. However, the dielectric constant relating to a (human) body can vary from patient to patient, and can even vary for the same patient over time. Therefore, it could be difficult to take into account, and it could be problematic to ignore, the effect of the dielectric material of the (human) body on the measurements of an attribute of a signal that was received after traveling through the dielectric material of the body.

It should be understood that when any of transmitter 102, receiver 104, antenna, adhesive, central unit and/or strap is described as "attached", "positioned", "placed" or similar, to the chest or chest wall, under the armpit, on a circumference of a chest wall, etc., the subject matter does not limit the manner of placement as long as the placement enables the signal path length to change when the chest moves during a breathing cycle. For example, any of the above may touch the skin of the patient, may touch a garment worn by the patient, may be integrated in a garment worn by the patient; may be integrated in an adhesive, strap, or central unit that touches the skin, touches a garment worn by the patient, or is integrated in a garment worn by the patent, etc. For another example, the placement may cause the signal to travel in a horizontal direction, in a vertical direction, diagonally, unevenly, up and down, and/or slanted, etc.

According to certain embodiments, multiple pairs of transmitter and receiver (and/or one or more sets of transmitter and corresponding multiple receivers and/or one or more sets of receiver and corresponding multiple transmitters) can be applied to make the measurement and calculation of volumetric changes more accurate.

It is to be understood that when it is stated that the volumetric change can be based on the change in signal path length during a time interval with reference to a difference in attribute of an (electronic) signal received by a receiver, the volumetric change can be based solely on the change in signal path length, or can also be based on other factors. The subject matter does not limit the other factors, but for the sake of further illustration to the reader some instances are now described. For instance, the volumetric change can be based on the change in path length of the signal received by the receiver, as well as the change(s) in path length(s) of one or more other (electronic) signal(s) received by the same and/or other receiver(s). Additionally or alternatively, the volumetric change can be based, for instance, on the change in path length of the signal received by the receiver during the time interval, as well as the change(s) in path length(s) of the signal received by the receiver during one or more other time interval(s) (and optionally the change(s) in path length(s) of one or more other signal(s) received by the same and/or other receiver(s) during the time interval and/or one or more other time interval(s)). Additionally or alternatively, for instance the volumetric change can be based on the change(s) in signal path length(s) with reference to attribute(s) of received signals, as well as on sound wave(s), and/or on change(s) in acceleration.

Figure 3:
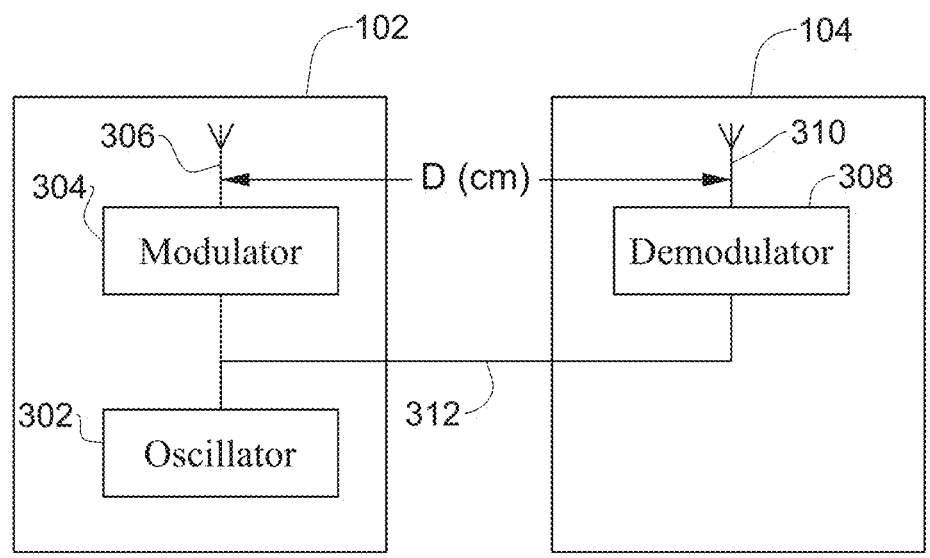
FIG. 3 is a functional block diagram schematically illustrating the functional structure of the transmitter and the receiver in accordance with certain embodiments of the presently disclosed subject matter.

Turning now to FIG. 3, there is shown a functional block diagram schematically illustrating the functional structure of the transmitter 102 and the receiver 104 in accordance with certain embodiments of the presently disclosed subject matter.

As shown, the transmitter 102 can comprise an oscillator 302, a modulator 304, and a transmitter antenna 306. The oscillator 302 is configured to generate a periodic, oscillating electronic signal, such as, e.g., a sine wave, which serves as a base signal before the modulation. By way of example, the oscillator 302 can be a RF oscillator that produces signals in the radio frequency range of 100 kHz to 100 GHz. For instance, the oscillator 302 can be configured to generate a base signal with predetermined frequencies such as, e.g., 2.4 GHz and 5 GHz. The determination of signal frequency is further described in detail with respect to FIG. 6.

The modulator 304 is configured to vary one or more properties of the base signal generated from the oscillator 102 with a modulating signal so that the modulated signal (i.e. the carrier signal) can be physically transmitted. Common modulation techniques that can be applied in the modulator 304 include Amplitude modulation (AM), Frequency modulation (FM), Phase modulation (PM), or any appropriate combinations thereof. By way of example, the modulator 104 can apply Quadrature amplitude modulation (QAM) scheme to the base signal for the purpose of easier phase extraction at the demodulator 308 of the receiver 104. The carrier signal can then be transmitted by the transmitter antenna 306 as electromagnetic waves to the receiver 104. The transmitter antenna 306 is designed to transmit the carrier wave with the predetermined frequency/ies.

The receiver 104 can comprise a demodulator 308 and a receiver antenna 310. The receiver antenna 310 receives the carrier signal transmitted from the transmitter antenna 306. The demodulator 308 is configured to extract the modulating signal from a modulated carrier wave. The demodulator applies a corresponding demodulation scheme in accordance with the modulation scheme applied at the modulator 304. The demodulator 308 is further configured to determine measurements of an attribute of the RF signal received at the beginning and the end of a time interval during the breathing cycle. As the received RF signal can refer to the modulated carrier signal (before demodulation) or the base signal (after demodulation), an attribute of a received signal for which a measurement is determined can be an attribute of the (modulated) carrier signal or of the base signal.

For simplicity's sake, it is assumed in the description herein that apparatus 100 includes a modulator 304 and a demodulator 308. However, it should be understood that in some embodiments, a signal can be transmitted without modulation, and in these embodiments the modulator 304 can be omitted. In these embodiments, the demodulator 308 may not perform demodulation but may still include functionality to determine measurements of an attribute of the signal received at the beginning and the end of a time interval during the breathing cycle, as described herein, mutatis mutandis.

According to certain embodiments, the attribute utilized for the measurement is the phase of the signal. Accordingly the demodulator 308 can comprise a phase detector or a phase comparator that can extract the phases of the signal at the beginning and end of the time interval. According to certain of these embodiments, the phase utilized for measurement can be the phase for different frequencies of the signal. Accordingly the demodulator 308 can comprise a detector or a comparator that can extract the relative phases of the signal at the beginning and end of the time interval.

According to certain other embodiments, the attribute utilized for the measurement can be time arrival of the signal. Accordingly the demodulator 308 can comprise a time of arrival detector or a time of arrival comparator that can extract time of arrival of the signal at the beginning and end of the time interval.

According to certain other embodiments, the attribute utilized for measurement can be the amplitude of the signal. Accordingly the demodulator 308 can comprise an amplitude detector or an amplitude comparator that can extract the amplitude of the signal at the beginning and end of the time interval. According to certain of these embodiments, the amplitude utilized for measurement can be the relative amplitudes of a set of frequencies of the signal (e.g. frequency with peak amplitude). Accordingly the demodulator 308 can comprise a detector or a comparator that can extract the relative amplitudes of the signal at the beginning and end of the time interval.

According to certain other embodiments, the attribute utilized for measurement can be the decay time of the signal. Accordingly the demodulator 308 can comprise a decay time detector or a decay time comparator that can extract the decay time of the signal at the beginning and end of the time interval.

According to certain other embodiments, the attribute utilized for measurement can be the degree of attenuation of the signal, time duration between transmission and reception of the signal, or any other difference between transmission and reception. Accordingly the demodulator 308 can comprise a degree of attenuation, time interval, or other difference detector or a degree of attenuation, time duration, or other difference comparator that can extract the degree of attenuation, time duration, or other difference for the signal at the beginning and end of the time interval.

In certain embodiments, the transmitter antenna 306 and the receiver antenna 310 can be modified spatially to reduce signal loss between the transmitter and receiver.

It is to be noted that each of the transmitter and the receiver can be self containable with all aspects needed to transmit and receive the unique RF signal, such as, e.g., a power source. As aforementioned, the processor and/or the I/O interface can be implemented in a stand-alone manner, or alternatively their functionalities can be integrated with, e.g., the receiver. By way of example, the calculated results can be sent to any desired media storage and display by way of wired or wireless communication.

According to certain embodiments, the receiver 104 can be connected with the transmitter 102 by a reference cable 312 that carries a reference signal. Specifically, the demodulator 308 of the receiver can be connected with the modulator 304 of the transmitter by the reference cable 312, as illustrated in FIG. 3, such that the demodulator can receive a reference signal that contains reference information of certain properties of the transmitted signal such as one or more transmitted signal attributes. By way of example, if the attribute utilized for the measurement is the phase of the signal, the demodulator can obtain the phase of the transmitted signal by detecting the (corresponding) phase of the reference signal. This is especially useful in cases where the oscillator 302 may generate an RF signal with random phase noises which vary at different time points. In such cases the received RF signal will also carry these phase noises which vary, e.g., at the beginning and the end of the time interval. In order to have accurate measurements of the phase of the RF signal received at the beginning and the end of the time interval, the phase noises that are included in the phases of the received RF signal have to be eliminated, for example, e.g. by subtracting the phase of the received RF signal with the phase of the reference signal.

According to certain embodiments, an attribute for which measurements are determined can relate to a difference between transmission and reception, such as degree of attenuation with respect to the transmitted signal, or time duration between transmission and reception. For instance, the measurements of degree of attenuation for the received signal can be determined at the beginning of the time interval and the end of the time interval. Determination of a measurement of such a difference attribute can require access to information regarding certain properties of the transmitted signal, e.g. by way of receiving via a reference cable 312 a reference signal that contains reference information of certain properties of the transmitted signal such as one or more transmitted signal attributes.

According to certain embodiments, the transmitter 102 and the receiver 104 may utilize antennas pre-fabricated to increase signal strength and reception. These antennas are commonly used in RF technology, however, they can be specifically adapted for attachment to the torso and the appropriate frequency and wavelength. According to certain embodiments, where the signal is guided through a strap rather than being wirelessly transmitted between antennas, the strap can extend between the positions shown in FIG. 3 for antennas 306 and 310, and antennas 306 and 310 can be omitted from the transmitter 102 and receiver 104 respectively.

Turning now to FIG. 5, there is shown a generalized flowchart of monitoring a volumetric change of a lung during a breathing cycle by using a RF signal, in accordance with certain embodiments of the presently disclosed subject matter.

A receiver (e.g., the receiver 104) receives (502) a RF signal transmitted from a transmitter. According to certain embodiments, the transmitter (e.g., the transmitter 102) can generate the RF signal and transmit it to the receiver. The transmitter and the receiver can be attached to a chest wall of the lung, or can be located anywhere else which enables calculation of a volumetric change of the lung during a breathing cycle.

The receiver further determines (504) measurements of an attribute of the RF signal received at the beginning and the end of a time interval during the breathing cycle. For instance, the time interval can be a fraction of the breathing cycle. By way of example, the time interval can be the period it takes for an individual to complete an inhalation, e.g., from the time the individual starts to inhale till the time that he has breathed in the maximum amount of air in the breathing cycle. By way of another example, the inhalation period can be divided to a few sub-periods and the time interval can be a sub-period of the inhalation period. For example, if the full inhalation period takes, e.g., one second to complete on average, the time interval can be set to be 0.1 second or 0.01 second. By way of another example, the time interval can be the period it takes for an individual to complete an exhalation, or a sub-period of the exhalation period. The selection of the time interval can be determined based on the accuracy required for the measurement.

Continuing with FIG. 5, a change in signal path length during the time interval can be calculated (506) by a processor (e.g., the processor 106) based on the measurements. As noted above, at least part of the signal path contours at least part of the chest. Any change in the signal path length during the breathing cycle can be assumed to be due to a change in the length of the at least part of the signal path that contours the at least part of the chest wall, because even if the signal path includes a part that does not contour the chest wall, the length of that part should not be affected by the breathing. Therefore, the calculation of the change in length of the signal path based on the measurements should be equivalent to a calculation of a change in distance between a transmitter 102 and receiver 104 attached on either end of the at least part chest wall contoured by the at least part of the signal path. In this case, the calculation of the change in distance can be based on measurements of an attribute of a signal received by the receiver 104 attached on the end of the at least part chest wall contoured by the at least part of the signal path, at the beginning and the end of a time interval.

For simplicity's sake it is assumed in the description below of FIGS. 4, 6, 7 and 10 that the least part of the signal path that contours at least part of the chest wall is on or beside at least part of a circumference of the chest wall, so that this at least part of the signal path can be said to be along (e.g. on or beside) at least part of the circumference of the chest wall. The term "circumference" (e.g. of the chest wall) is used to refer to the path around (e.g. the chest wall), and the term "length of circumference" or "circumference length" is used to refer to the length of the path. Therefore, using this assumption, the calculation of the change in length of the signal path based on the measurements should be equivalent to a calculation of a change in distance between a transmitter 102 and receiver 104 positioned on the circumference of the chest wall, on either end of the at least part of the circumference along which the at least part the signal path is assumed to be. In this case, the calculation of the change in distance can be based on measurements of an attribute of the signal received by the receiver 104 positioned on the circumference, at the beginning and the end of a time interval. Due to the equivalence of calculating the change in distance to calculating the change in signal path length, it is assumed in the description below of FIGS. 4, 6, 7, and 10 that the transmitter 102 and the receiver 104 are positioned on the circumference of the chest wall, on either end of the at least part of the circumference along which the at least part the signal path is assumed to be, disregarding whether or not the transmitter 102 and receiver 104 are actually positioned in this manner. The change in distance between the transmitter 102 and the receiver 104 can be said, under this assumption, to be along the circumference. The signal can travel, for instance, through a strap between the transmitter 102 and the receiver 104 located at the two ends of the strap, or the signal can travel, for instance, wirelessly (e.g. via an air channel) between the transmitter 102 and the receiver 104 which are located at the two ends of the air channel.

It is to be noted that the subject matter does not limit the calculation of the change in the signal path during the time interval based on the measurements, and therefore the calculation can vary depending on the attribute, and/or for any other reason. However for the sake of further illustration, FIGS. 6, 7, and 10 illustrate certain embodiments of the calculation.

As aforementioned, according to certain embodiments, the RF signal can be a single carrier signal characterized by a certain carrier wavelength or a certain frequency. Although as mentioned above the RF signal need not be a carrier signal, for simplicity's sake FIG. 6 is described with reference to a single carrier signal characterized by a carrier wavelength. According to certain embodiments, the single carrier signal can be selected such that the wavelength of the signal is greater than twice a change in the signal path length during the time interval, as will be explained in detail with reference to FIG. 6.

Attention is now directed to FIG. 6, illustrating an exemplified single carrier signal in a sine waveform utilized in the transmitter and the receiver in accordance with certain embodiments of the presently disclosed subject matter.

A single carrier signal such as the sine wave is a periodic waveform that repeats itself every period of time. By way of example, a sine wave can be represented as a function of time (t) as:

$$y(t)=A(\sin 2\pi f t+\theta')$$

Where:

A is the amplitude that is the peak deviation of the function from zero;

f is the frequency that represents the number of oscillations (cycles) that occur each second of time; and θ is the phase which defines the position of a point in time on a waveform cycle, measured as an angle in degrees or radians.

Another parameter of the sine signal which is not shown in the above function is the wavelength λ. Wavelength is the spatial period of the sine wave: the distance over which the wave's shape repeats in a position axis. It can be determined by considering the distance between consecutive corresponding points of the same phase, such as the distance between two zero-crossings as illustrated in FIG. 6. The wavelength λ of a sine wave traveling at constant speed v is determined by: λ=v/f. As shown, it is clear that the sine signal travels a distance of a wavelength λ every period of time, and the phase of the signal repeats its value every wavelength λ. Thus the value of the phase has a linear mapping (also referred to as linear correlation) relationship with a respective point within a wavelength on the position axis: (0 ... 2π) as to (0 ... λ). Similarly, this linear mapping relationship between phase and distance can be utilized in order to measure the change in distance between the transmitter and the receiver during the time interval, as long as the change in distance is within half the wavelength of the signal. This ensures that by measuring the phase of the received signal, the change in distance can always be calculated explicitly and unambiguously based on the linear mapping relationship. For instance, in order to measure the change of distance Δd in the range of 1 mm, it is needed to select a wavelength that is in a similar range and greater than 2Δd, such as, for example, 1 cm. This means that the RF signal should be selected to have a signal frequency of 30 GHz.

By way of example, continuing with the exemplified illustration in FIG. 6, assuming that a transmitter 102 is positioned at the origin of a position axis, and transmits a single carrier signal: A(sin 2πft) (with a phase θ=0). According to the linear mapping relationship described above, the phase accumulated at a certain position x (x is the distance, along the signal path away from the origin of the wavelength) is determined as: θ=2πx/λ. Thus a receiver 104 which is positioned at a distance of D along the circumference from the transmitter receives the transmitted signal as: A sin(2πft+2πD/λ). Assuming at a time point t1, the distance along the circumference between the transmitter and the receiver is D1 and the received signal is: A sin(2πft+2πD1/λ). After a certain time interval Δt, the distance along the circumference between the transmitter and the receiver at t2 is D2 and the received signal is: A sin(2πft+2πD2/λ). Thus the difference between the phase of the received signal at t1 and t2 is 2π(D2−D1)/λ. By calculating the difference between measurements of the phase at t1 and t2, e.g., θ2−θ1, the change of distance along the circumference Δd=D2−D1 can be calculated accordingly as (θ2−θ1)*λ/2π.

For instance, as shown in FIG. 6, the phase of the received signal at a time point t1 is 3π, and the phase of the received signal at a time point t2 is 3.5π. Accordingly the difference between measurements of the phase at t1 and t2 is 3.5π−3π=0.5π. The change of distance along the circumference Δd can be calculated as 0.5π*λ/2π=0.25λ.

Turning now to FIG. 7, there is shown a schematic illustration of a UWB signal in time domain and frequency domain in accordance with certain embodiments of the presently disclosed subject matter.

As aforementioned, according to certain embodiments the RF signal can be a UWB signal. The UWB signal can be characterized by an ultra-wide bandwidth exceeding 500 MHz, and the frequency range can extend from 3.1 GHz to 10.6 GHz, as shown in the frequency domain illustration of FIG. 7. Commonly, impulse radio (IR) systems, which transmit very short pulses with a low duty cycle, are employed to implement UWB systems, as shown in the time domain illustration of FIG. 7. In such systems, a train of pulses is sent and information is usually conveyed by the position of the pulses. The ultra-wide bandwidth of UWB signals implies a high time resolution which facilitates precise positioning applications based on Time-of-Arrival (TOA) measurements. By way of example, assuming a transmitter 102 of apparatus 100 transmits a UWB signal comprising a train of pulses, the receiver 104 which is positioned at a distance of D1 along the circumference from the transmitter receives a transmitted pulse at time-of-arrival t1=D1/C wherein C is the speed of light. After a certain time interval in the breathing cycle, the receiver 104 is now positioned at a distance of D2 along the circumference from the transmitter, and the receiver receives a second transmitted pulse at time-of-arrival t2=D2/C. Thus Δt=t2−t1=(D2−D1)/C=Δd/C. Accordingly by determining the measurements of the time-of-arrival of two pulses t1 and t2 and the time interval Δt in between, the change of distance Δd along the circumference can be calculated as Δd=Δt*C.

Figure 10A:
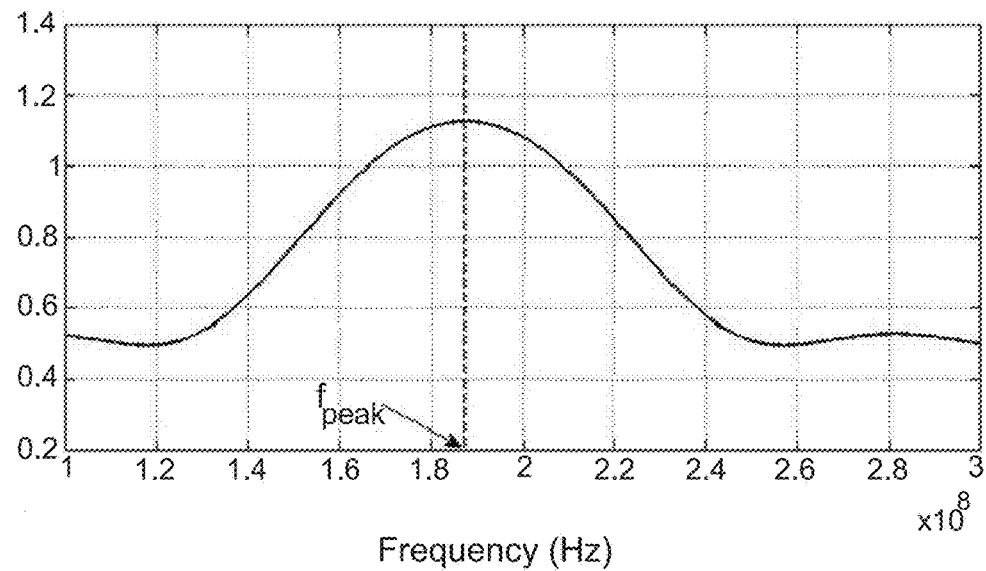
FIG. 10A and FIG. 10B (collectively FIG. 10) illustrate an example of the absolute values of a frequency response of a strap in accordance with certain embodiments of the presently disclosed subject matter.
Figure 10B:
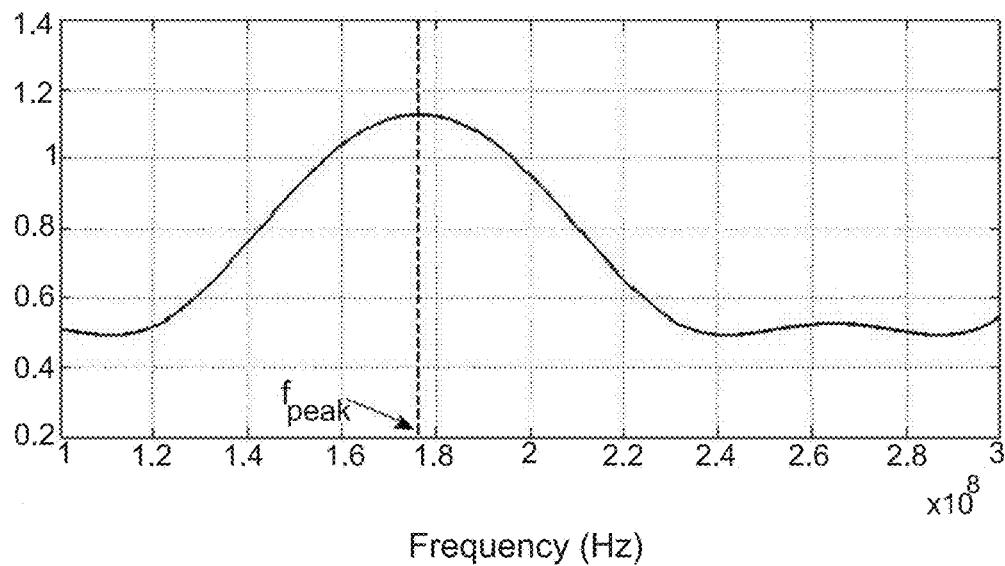

According to certain embodiments the RF signal can be a wideband signal characterized by a bandwidth of 0.1 Mhz to 200 Mhz, and the frequency range can extend from 100 Mhz to 10 Ghz. Referring now to FIGS. 10A and 10B, the transmitter 102 can generate a transmitted signal whose spectrum is given by X(f), where most of the energy of X(f) is inside the range: $f_{min} < f < f_{max}$.

As is true for other signals described herein, the transmitted signal whose spectrum is given by X(f), can flow from the transmitter 102 to the receiver 102 both of which are positioned on the circumference, through a strap or via an air channel (for wireless transmission). The frequency response of the received signal can be denoted by Y(f). The receiver can calculate the frequency response H(f) of the strap or of the air channel by:

$$H(f) = \frac{Y(f)}{X(f)} \text{ for every } f_{min} < f < f_{max}.$$

The frequency response H(f) of the strap or of the air channel, can be highly correlated to the length of the strap or to the length of the air channel. Therefore the relative amplitudes for a set of frequencies or phase for different frequencies can serve as an indication of the length of the strap or air channel. Referring to relative amplitudes for a strap, the receiver 104 can determine a measurement of amplitude of each frequency in the set of frequencies relative to amplitudes of other frequencies in the frequency set. The receiver 104 can then detect the frequency in which the amplitude of the frequency response of the strap is maximized. The length of the strap can be based on the measurement of the relative amplitudes, e.g. by being a function of the frequency in which the amplitude of the frequency response of the strap is maximized. In this example, the length of the strap can be calculated (by way of example) as follows:

$$\hat{L} = \frac{\lambda_{peak}}{2} = \frac{C}{2f_{peak}}$$

where $\hat{L}$ is the estimation of the length of the strap, $f_{peak}$ is the frequency in which the amplitude of the frequency response H(f) is maximized, C is the speed of light, and $\lambda_{peak}$ is the wavelength at the frequency of the peak.

Therefore the change in distance Δd along the circumference of the chest, between the transmitter 102 and the receiver 104, can be calculated as $$L2 - L1 = \frac{C}{2f_{peak2}} - \frac{C}{2f_{peak1}}.$$

FIG. 10A illustrates an example of the absolute values of a frequency response of a strap, in accordance with certain embodiments of the presently disclosed subject matter. FIG. 10A depicts the frequency response when the length of the strap is minimized, assumed to be at point t1. The frequency with the peak amplitude (also referred to as peak-amplitude frequency, herein), shown by the dashed line in FIG. 10A to be about 185 MHz, represents the frequency in which the absolute value of the frequency response is maximized FIG. 10B illustrates another example of the absolute values of a frequency response of a strap, in accordance with certain embodiments of the presently disclosed subject matter. FIG. 10B depicts the frequency response when the length of the strap is maximized, assumed to be at point t2. The frequency with the peak amplitude, shown by the dashed line in FIG. 10B to be about 175 MHz, represents the frequency in which the absolute value of the frequency response is maximized. Therefore the change in distance Δd along the circumference, assuming frequencies with peak amplitude as in FIGS. 10A and 10B can be calculated as $$\frac{C}{2*175*10^6} - \frac{C}{2*185*10^6}$$

For an air channel, the receiver 104 can determine measurements of phase for different frequencies. For example the receiver can determine measurements of phase for different frequencies, and thus the changes in phase for the different frequencies during a time interval. Continuing with this example, and referring for simplicity's sake to two frequencies, say 200 MHz and 205 MHz, assume that at the beginning of the time interval the phase for H(f) at 200 MHZ is 150 degrees and at 205 MHz the phase for H(f) is 160 degrees. Similarly, assume that at the end of the time interval, the phase of H(f) is 150.5 degrees at 200 MHz and 160.51 degrees at 205 MHz. The 0.5 degrees change at 150 MHZ and 0.51 change at 160 MHZ can be used to estimate changes in distance along the circumference for the various changes in phase with respect to the frequencies, e.g. by substituting 0.5 degrees and 0.51 degrees for (θ2−θ1) in the equation (θ2−θ1)*λ/2π. The value of Δd along the circumference of the chest, between the transmitter 102 and the receiver 104, can be calculated, for instance, as the average of these changes in distance.

In other embodiments, the receiver 104 can determine for the strap measurements of phase for different frequencies, and/or can determine for the air channel relative amplitudes of a set of frequencies.

Turning back to FIG. 5, after the change in distance Δd along the circumference is obtained, for example as described above with reference to any of FIG. 6, 7, or 10, the processor is further configured to calculate (508) the volumetric change of the lung during the time interval based on the change in distance Δd. The calculation of the volumetric change based on the change of distance is further described with reference to FIG. 4.

Figure 4:
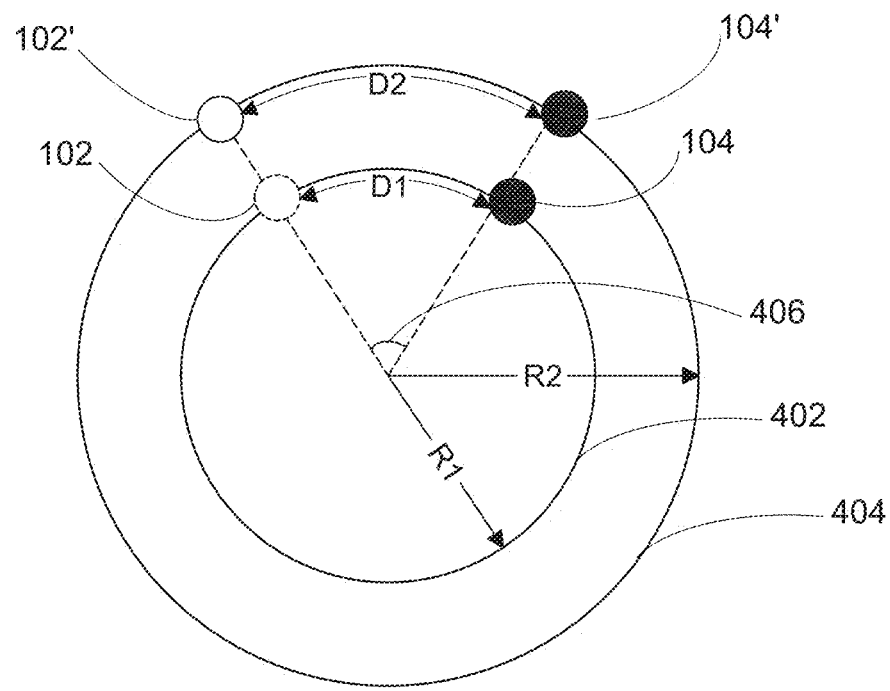
FIG. 4 illustrates an exemplified top view of a lung when looking at it from above the lung in accordance with certain embodiments of the presently disclosed subject matter.

Attention is now drawn to FIG. 4, illustrating an exemplified top view of a lung when looking at it from above the lung in accordance with certain embodiments of the presently disclosed subject matter. When a person breathes, the lung is able to expand and contract to some degree through the use of the respiratory muscles. As a result, air is transported into or expelled out of the lung. Accordingly, the transmitter 102 and the receiver 104 that are attached to the chest wall of the lung are also moving outwards and inwards during inhalation and exhalation of the breathing process.

As illustrated in FIG. 4, continuing with the assumption that the lung is in the shape of a ball, at an initial time point of t1, an initial size of the lung is shown as the inner ball 402, with a radius of R1. The volume of the inner ball 402 is: $V1=4\pi R1^3/3$, A pair of transmitter and receiver are placed on the inner ball 402 at their initial positions 102 and 104. The distance along the circumference between 102 and 104 is marked as D1. Assuming the person is in an inhalation process, the lung is expanding from the size of the inner ball 402 to the size of the outer ball 404 with a radius of R2 after a certain time interval Δt. The volume of the outer ball 404 is: $V2=4\pi R2^3/3$, Accordingly the transmitter and the receiver move to the respective positions of 102' and 104' on the outer ball 404 at a time point of t2 (t2=t1+Δt). The distance along the circumference between 102' and 104' is marked as D2. Thus the relative position change Δd, along the circumference, between the transmitter and the receiver at t1 and t2 is Δd=D2−D1. D1 and D2 can be calculated based on R1 and R2 in accordance with the angle 406 formed between the two connecting lines of the transmitter and the receiver to the center of the ball. By way of example, if the angle 406 is 90 degrees, D1=π/2*R1, and D2=π/2*R2. Thus Δd=π/2*(R2−R1). The volumetric change dV between t2 and t2 is:

$$dV = V2 - V2 = \frac{4\pi R_2^3}{3} - \frac{4\pi R_1^3}{3} = \frac{4\pi}{3}(R_2^3 - R_1^3)$$

Thus the relationship between the volumetric change ΔV and the relative position change Δd can be written as:

$$\Delta V = \frac{4\pi}{3}\left(\left(\Delta d\frac{2}{\pi} + R_1\right)^3 - R_1^3\right)$$

The value of Δd that can be substituted in the above equation can be, for example any of the Δd's calculated above with reference to any of FIG. 6, 7, or 10 or a Δd calculated using a different calculation. For estimating ΔV in the above equation, the value of $R_1$ can be substituted with a certain nominal value, e.g. 14.3 cm for an adult man. Alternatively, the nominal value can be estimated, for example, by measuring the circumference of the patient prior to monitoring, and dividing by 2π.

It is to be noted that D1 and D2 are measured along a curved line connecting between transmitter 102 and the receiver 104, which is always larger than the straight line connecting these points, and this allows an error in Δd to have less of an effect on volume than if the signal traveled in a straight line (e.g. through the body) between the transmitter 102 and the receiver 104. To illustrate this, assume an alternative scenario where a signal would travel in a straight line (through the body), and the angle would still be 90 degrees. In this scenario, the change in distance would equal $\sqrt{2}(R2-R1)$. The volume in the alternative scenario would equal $$\Delta V = \frac{4\pi}{3}\left(\left(\Delta d/\sqrt{2}+R_1\right)^3 - R_1^3\right).$$

In this scenario an error in change in distance Δd would have a greater impact on volume (since $1/\sqrt{2}$ is greater than 2/π). For a larger angle, the difference in impact on volume between an error in change in distance where the signal travels in a straight line and an error in change in distance along the circumference would be even greater, meaning that the volume would be even more adversely affected by an error in distance where the signal travels in a straight line.

It is further to be noted that the shape of the lung can be assumed to be in other suitable geometric models other than a ball, such as semi sphere, etc, and the placement of the transmitter 102 and the receiver 104, the calculation of Δd and the calculation of volumetric change can be adapted in accordance with respective shape models.

Those versed in the art will readily appreciate that the examples illustrated with reference to FIGS. 4, 6, 7 and 10 are by no means inclusive of all possible alternatives but are intended to illustrate non-limiting examples, and accordingly other ways of calculation and determining measurements can be used in addition to or in lieu of the above. For example, in certain embodiments, a calibration table can be used in addition to or instead of equations, such as a table which associates length of strap to peak-amplitude frequency.

According to certain embodiments, there may be signal interference when, e.g., applying multiple pairs of transmitter and receiver or multiple transmitters and one receiver on the chest wall. This can be solved, for instance, by using Frequency-division multiple access (FDMA) or Time-division multiple access (TDMA). With FDMA the pairs of transmitter and receiver can operate simultaneously and each signal uses a separate frequency sub-band, while with TDMA the pairs can operate one after another and each signal appears on the line only a fraction of time in an alternating pattern. One advantage of using TDMA is that only a single signal source is needed for all the pairs thus the bill of materials (BOM) will be relatively lower.

As stated above, an electronic signal in accordance with the presently disclosed subject matter does not necessarily have to an RF signal. Referring again to the example given above of a square wave which changes every 2 msec from +5V to 0V or vice versa, the attribute that can be utilized, can be for example, the time of arrival.

Another attribute that can be used for this signal (and/or for other signals, including RF signals) is the decay time. Assume here as above, for simplicity's sake, that the transmitter 102 and the receiver 104 are positioned on the circumference of the chest wall, and the signal travels between the transmitter 102 and the receiver 104 via a strap. It is expected that in response to a sharp drop of the transmitted voltage from 5V to 0V, the received signal will decay gradually from its peak (which may be denoted as $V^+$) toward zero volts. Typically, this decay over time has the form of:

$$V(t)=V^+e^{-\gamma t},$$

where t is the time since the beginning of the voltage drop at the receiver. The beginning of the voltage drop can be defined, for example, as the time in which the voltage reached $0.98V^+$. The constant γ is typically related to the resistance, capacitance and inductance of the strap. In some cases the capacitance or the inductance may be linearly related to the length of the strap. Hence, in some cases the voltage decay may have the form of $V(t)=V^+e^{-\alpha L t}$, where L is the length of the strap and α is constant.

By monitoring V(t) it is possible to measure changes in the strap length. For example, a target voltage $V_T$ (e.g. 1 volts) can be chosen and the time t (measured from the beginning of the drop) found in which $V(t)=V_T$. This time can be termed the "decay time". By measuring the decay time, the change in the strap length can be determined. For example, if $t_1$ denotes the decay time at the beginning of the time interval and $t_2$ denotes the decay time at the end of the time interval, the change in distance Δd along the circumference of the chest, between the transmitter 102 and the receiver 104, can be calculated as:

$$\Delta d = \frac{L(t_1 - t_2)}{t_2},$$

where L is the nominal strap length. The nominal strap length can be found e.g. by measuring the strap length at the beginning of the monitoring period, while the patient is wearing the strap. This Δd can be substituted into the equation for calculating ΔV discussed above.

In accordance with certain embodiments, the apparatus 100 (e.g. the processor 106) can be configured to calculate tidal volume for a breathing cycle. Tidal volume is the difference between the maximum volume and the minimum volume during a breathing cycle. For example, the tidal volume can be calculated as follows. Assume for simplicity's sake that a time interval is smaller than the period of a breathing cycle, and therefore the volumetric change during a time interval is representative of a change over a smaller duration of time than the period of the breathing cycle. The first alternative for calculating a possible tidal volume can include summing the volumetric changes for a plurality of time intervals starting with the first negative volumetric change during a breathing cycle (indicative of the maximum volumetric change having been reached) and ending with the volumetric change immediately preceding the first positive volumetric change in the breathing cycle (indicative of the minimum volumetric change having been reached). The second alternative for calculating a possible tidal volume can include summing the volumetric changes for a plurality of time intervals starting with the first positive volumetric change during a breathing cycle (indicative of the minimum volumetric change having been reached) and ending with the volumetric change immediately preceding the first negative volumetric change in the breathing cycle (indicative of the maximum volumetric change having been reached). The tidal volume can equal the higher of the two alternative sums. If a time interval is instead equal to, or longer than the period of the breathing cycle, then the calculation of tidal volume can be adapted accordingly.

Figure 11:
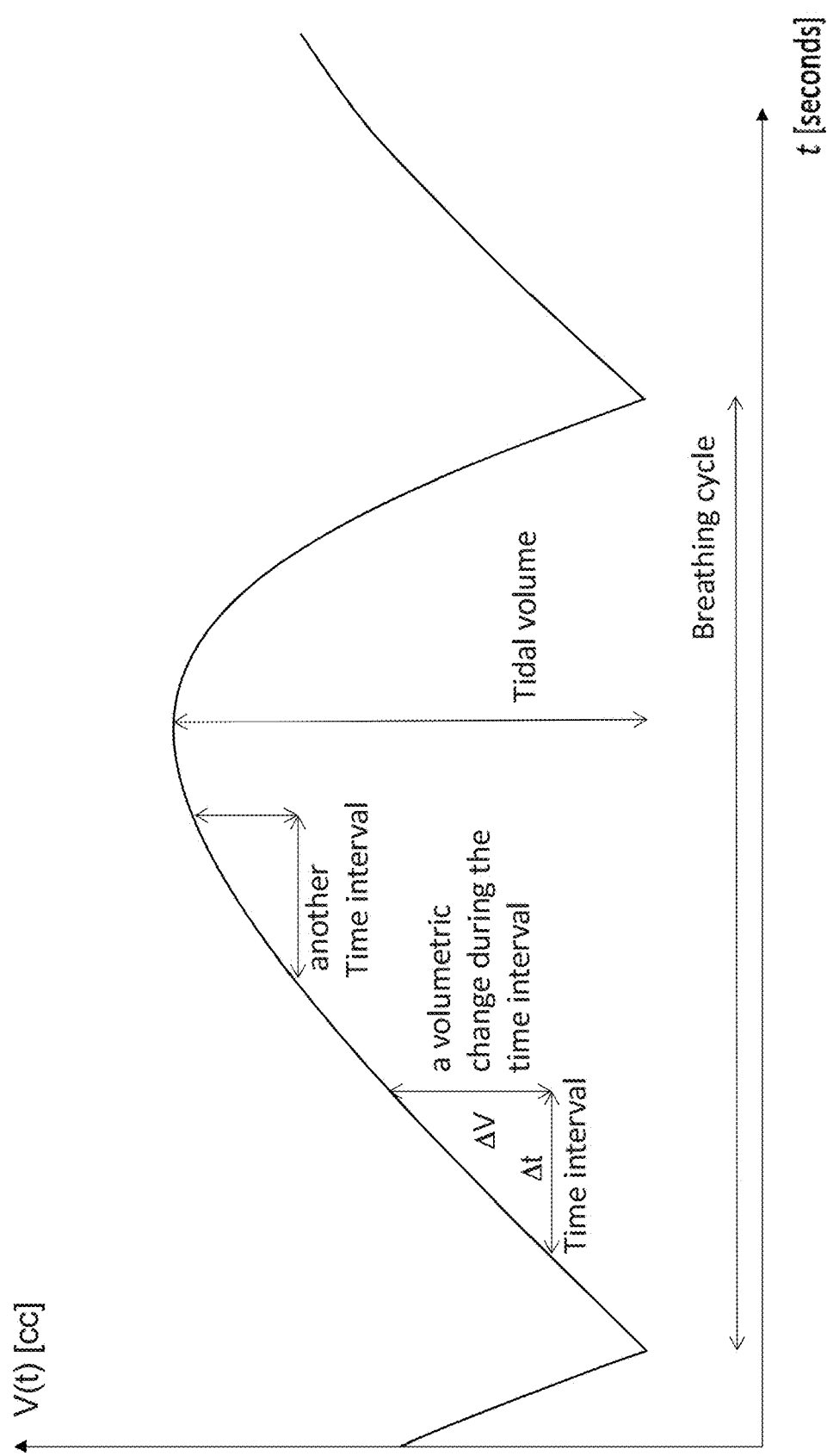
FIG. 11 is a graph of volume versus time during a breathing cycle in accordance with certain embodiments of the presently disclosed subject matter.

Optionally, calculated volumetric change(s) during a breathing cycle can be used to construct a graph of volume versus time for the breathing cycle. FIG. 11 is a graph of volume versus time during a breathing cycle in accordance with certain embodiments of the presently disclosed subject matter. Such a graph may facilitate, for instance, calculation of the tidal volume by apparatus 100, detection of breathing patterns by apparatus 100, and/or understanding by a user that views the graph.

In accordance with certain embodiments, the apparatus 100 (e.g. the processor 106) can be configured to detect a breathing pattern from a set of pre-defined breathing patterns. For instance, the set may include pathological breathing patterns.

Consider that in bronchospasm or asthma or chronic obstructive pulmonary disease (COPD) because of obstruction, the inspiratory stage (also referred to an inhalation period) may be shorter than normal, and the expiratory stage (also referred to as exhalation period) may be longer than normal. To detect these differences in stage lengths, the apparatus 100 (e.g. processor 106) can in some examples be configured to estimate the rate of inhaling by estimating the derivative of lung volume vs. time, and determine if the derivative is larger than a certain threshold. This can be written as:

$$\frac{dv(t)}{d(t)} > A,$$

where A is some positive threshold. Optionally, an alarm can be generated if the derivative is larger than the threshold.

The apparatus 100 (e.g. processor 106) can be configured to estimate the derivative $$\frac{dv(t)}{d(t)},$$

by choosing a relatively short time interval $\Delta t$, and calculating the volumetric change during the time interval $\Delta V$ as discussed above. The calculated volumetric change $\Delta V$ can then be divided by the time interval $\Delta t$. In other words, the derivative can be estimated by:

$$\frac{dv(t)}{dt} \approx \frac{\Delta V}{\Delta t}.$$

Therefore the alarm can optionally be generated if $$\frac{\Delta V}{\Delta t} > A$$

Additionally or alternatively, the apparatus 100 (e.g. processor 106) can in some examples be configured to check if the expiatory stage is longer than normal, by detecting such cases when $t_{min} - t_{max} > T_t$, where $t_{max}$ is the time when the volume is maximized during a breathing cycle, $t_{min}$ is the first time after $t_{max}$ in which the volume is minimized, and $T_t$ is some threshold time. To find $t_{max}$ and $t_{min}$ the apparatus 100 (e.g. processor 106) can be configured, for example, to find the time in which the derivative $$\left(\text{approximated by} \frac{\Delta V}{\Delta t}\right),$$

changes from positive to negative and from negative to positive respectively.

In any of these examples, $$\frac{dv(t)}{dt} \left(\text{or the approximation of} \frac{\Delta V}{\Delta t}\right)$$

can optionally be calculated for a plurality of time intervals (e.g. repeatedly or periodically) thus providing a breathing pattern. The breathing pattern can be considered to be based on the volumetric changes during these time intervals, e.g. because the breathing pattern can be provided by dividing these volumetric changes by the respective time intervals. For example, $$\frac{dv(t)}{dt} \left(\text{or the approximation of} \frac{\Delta V}{\Delta t}\right)$$

can be calculated, say over 100 breathing cycles.

The apparatus 100 (e.g. processor 106) can be configured to monitor the breathing pattern. For example, the apparatus 100 (e.g. processor 106) can be configured to detect if the monitored breathing pattern is a breathing pattern selected from a predefined set of breathing patterns. For instance, assume that one of the predefined breathing patterns in the set is a breathing pattern for COPD. Further assume that the breathing pattern for COPD is a breathing pattern in which the average of $$\frac{\Delta V}{\Delta t}\text{'s}$$

calculated over, say, 100 breathing cycles, is above a threshold, or in which the number of times that $$\frac{\Delta V}{\Delta t}$$

is above a threshold, say during 100 breathing cycles, is above a certain number. In this instance, the apparatus 100 can detect that the breathing pattern is a COPD breathing pattern by determining that the condition(s) of a COPD breathing pattern is/are met.

Upon detection of a breathing pattern selected from a predefined set of breathing patterns, an alarm can optionally be generated.

A breathing pattern can give the physician or other health professional information regarding the disease process and guide treatment. The breathing pattern can additionally or alternatively be used, to assess response to treatment.

In accordance with certain embodiments, the apparatus and method described above can be adapted to also take into account a sound wave, transmitted for example between the same or a different transmitter than discussed above and the same or different receiver than discussed above. The transmitter can generate a unique tone such as through a speaker and the receiver can receive the sound wave through a microphone. By determining measurements of the time for the sound wave to pass from the transmitter to the receiver, the change in distance between the transmitter and the receiver can be calculated thus inferring chest expansion and calculating a change in volume of breathing.

In accordance with yet further embodiments, the apparatus and method described above can be adapted to also take into account a multitude of accelerometers attached to the chest wall. By measuring changes in acceleration, changes in the distance between the accelerometers can be computed, reflecting volumetric changes.

Accelerometers have been used as position sensors in inertial navigation systems for many years. By way of example, inertial navigation systems use a combination of accelerometers and gyroscopes to determine position by means of "dead reckoning," where the deviation of position from a known reference (or starting point) is determined by integration of acceleration in each axis over time.

If the apparatus is configured to calculate a volumetric change based on change(s) in signal path length(s) as discussed above and to calculate a volumetric change based on the change(s) in distance(s) between transmitter(s) and receiver(s) of sound wave(s) and/or based on changes in the distance(s) between accelerometers, the apparatus can calculate the volumetric change by using any methodology to combine and/or prioritize the various possibilities for calculating the volumetric change.

According to certain embodiments, there is also provided a wearable device integrating the apparatus 100 or a part thereof and its functionality as described with reference to FIG. 1 and/or elsewhere herein. According to further embodiments, there is further provided a wearable device operating in accordance with the method as described with reference to FIG. 5 or a part of this method, and/or as described elsewhere herein. By way of example, the wearable device can be implemented as a wearable garment or wearable strap worn by a patient that (e.g. periodically or repeatedly) calculates a volumetric change of the lung of the patient.

Although the description above focuses on determining measurements of an attribute, calculating a change in signal path length, and calculating a volumetric change, in accordance with certain embodiments the apparatus and method described above can be adapted to detect a breathing pattern, from a set of pre-defined breathing patterns, without necessarily calculating a volumetric change. The set of pre-defined breathing patterns can include pathological breathing patterns. It is noted that during breathing the chest expands and contracts causing an increase or decrease respectively in the circumference of the chest, but also the diaphragm muscle expands and contracts causing an increase or decrease respectively in circumference of the abdomen. In pathological conditions such as asthma, COPD, or congestive heart failure (CHF), the breathing pattern will become abnormal due to the change in the ratio between chest and abdominal breathing caused by the increase in the abdominal component. To detect this abnormal breathing pattern, a minimum of two straps can be used, for example with one attached to the chest and one attached to the abdomen (reflecting the contribution of the diaphragm in breathing). The straps may or may not share the same transmitter 102 and/or receiver 104. The changes in the lengths of the two straps (indicative of changes in signal path length) can be calculated for a plurality of time intervals. For example, ignoring any difference between length of signal path and length of strap for simplicity's sake, the changes in lengths can be based on measurements of attributes as discussed above. Based on the changes in lengths, apparatus 100 (e.g. processor 106) can be configured to calculate the maximal change in length for each of the straps during a breathing cycle. For instance, the maximal change in length during a breathing cycle for the abdominal and chest belt can be denoted as $\Delta L_{ab}$ and $\Delta L_{ch}$ respectfully. For detecting pathological conditions such as asthma, COPD, CHF, the processor can, for example calculate the ratio between $\Delta L_{ab}$ and $\Delta L_{ch}$ and determine if $$\frac{\Delta L_{ab}}{\Delta L_{ch}} > K$$

where K is some pre-defined threshold. Optionally an alarm can be generated if the threshold is exceeded. Optionally, the apparatus 100 (e.g. processor 106) can be configured to calculate the maximal changes in lengths and the ratio between them over a plurality of breathing cycles (e.g. repeatedly or periodically performing the calculation) and thus a breathing pattern can be provided. The apparatus 100 (e.g. processor 106) can be configured to monitor the breathing pattern. For example, the apparatus 100 (e.g. processor 106) can be configured to detect a breathing pattern from a set of predefined breathing patterns, when matching (e.g. abnormal breathing pattern). Upon detection, an alarm can optionally be generated. The breathing pattern can give the physician or other health professional information regarding the disease process and guide treatment. The breathing pattern can additionally or alternatively be used to assess response to treatment.

It is to be understood that the presently disclosed subject matter is not limited in its application to the details set forth in the description contained herein or illustrated in the drawings. The presently disclosed subject matter is capable of other embodiments and of being practiced and carried out in various ways. Hence, it is to be understood that the phraseology and terminology employed herein are for the purpose of description and should not be regarded as limiting. As such, those skilled in the art will appreciate that the conception upon which this disclosure is based can readily be utilized as a basis for designing other structures, methods, and apparatuses for carrying out the several purposes of the present presently disclosed subject matter.

It will also be understood that the apparatus according to the presently disclosed subject matter can be implemented, at least partly, as a suitably programmed computer. Likewise, the presently disclosed subject matter contemplates a computer program being readable by a computer for executing the disclosed method or a part thereof. The presently disclosed subject matter further contemplates a machine-readable memory tangibly embodying a program of instructions executable by the machine for executing the disclosed method or a part thereof.

The invention claimed is:

1. A method of monitoring volumetric change of a lung during a breathing cycle by using an electronic signal, the method comprising:
receiving by a receiver an electronic signal transmitted from a transmitter, wherein a path of the signal contours at least part of a circumference of a chest wall of the lung;
determining by the receiver measurements of an attribute of the signal received at the beginning and the end of a time interval during the breathing cycle;
calculating by a processor a change in length of the signal path during the time interval based on the measurements of the attribute of the signal received at the beginning and the end of the time interval; and
calculating by the processor a volumetric change during the time interval based on the change in signal path length.

2. The method of claim 1, wherein the electronic signal is a radio frequency (RF) signal.

3. The method of claim 2, wherein the signal is a single carrier RF signal characterized by a carrier wavelength.

4. The method of claim 3, wherein the single carrier signal is selected such that the carrier wavelength is greater than twice the change in signal path length during the time interval.

5. The method of claim 3, wherein the attribute is phase of the single carrier signal.

6. The method of claim 1, wherein the signal flows from the transmitter to the receiver through a belt or a strap or a band attached to the chest wall of the lung.

7. The method of claim 1 wherein the change in signal path length is in a linear correlation relationship with the measured difference.

8. The method of claim 1, wherein the attribute is amplitude of the signal.

9. The method of claim 8, wherein said signal is characterized by a predetermined set of frequencies, and wherein said amplitude is an amplitude of each frequency in the set of frequencies relative to amplitudes of other frequencies in the frequency set.

10. The method of claim 1 wherein said determining measurements, calculating a change in signal path length, and calculating a volumetric change are performed for a plurality of time intervals.

11. The method of claim 1, wherein said signal is an Ultra-wide Band (UWB) RF signal characterized by a bandwidth which is larger than 500 Mhz.

12. The method of claim 1, wherein said attribute is time-of-arrival of the signal.

13. The method of claim 1, wherein the transmitter and the receiver are positioned on the circumference of the chest wall.

14. The method of claim 1, wherein the time interval is a fraction of the breathing cycle.

15. The method of claim 1, wherein the receiver is connected to the transmitter by a reference cable that carries a reference signal, a corresponding attribute of the reference signal being indicative of an attribute of a transmitted signal.

16. The method of claim 1, further comprising: calculating by the processor a tidal volume for the breathing cycle.

17. The method of claim 16, the method further comprising: measuring a respiratory rate; and generating an alarm if the tidal volume is within a pre-specified range, and the respiratory rate is normal.

18. The method of claim 16, further comprising: generating a first indication if the tidal volume is below a first threshold, and generating a second indication if the tidal volume is above a second threshold, wherein the second threshold is larger than the first threshold and a difference between the first and second threshold is below 10% of normal tidal volume.

19. The method of claim 1, wherein the processor is a part of the receiver.

20. The method of claim 1, further comprising: performing said determining measurements, calculating a change in signal path length, and calculating a volumetric change for a plurality of time intervals, and detecting a breathing pattern, from a set of pre-defined breathing patterns, based on volumetric changes during the plurality of time intervals.

21. An apparatus capable of monitoring a volumetric change of a lung during a breathing cycle by using an electronic signal, the apparatus comprising at least one transmitter and a receiving module, the receiving module including at least one receiver operatively connected to a processor, wherein:
the at least one transmitter is configured to transmit the electronic signal, wherein a path of the signal contours at least part of a circumference of a chest wall of the lung;
the at least one receiver is configured to:
receive the electronic signal transmitted from the at least one transmitter, and determine measurements of an attribute of the signal received at the beginning and the end of a time interval during the breathing cycle;
the processor is configured to:
calculate a change in length of the signal path during the time interval based on the measurements of the attribute of the signal received at the beginning and the end of the time interval; and
calculate the volumetric change of the lung during the time interval based on the change in signal path length.

22. The apparatus of claim 21, wherein the electronic signal is an RF signal.

23. The apparatus of claim 21, wherein the signal is a single carrier RF signal characterized by a carrier wavelength.

24. The apparatus of claim 23, wherein the single carrier signal is selected such that the carrier wavelength is greater than twice the change in signal path length during the time interval.

25. The apparatus of claim 23, wherein said attribute is phase of the single carrier signal.

26. The apparatus of claim 21, wherein the signal flows from the transmitter to the receiver through a belt or a strap or a band attached to the chest wall of the lung.

27. The apparatus of claim 21, wherein said change in signal path length is in a linear correlation relationship with a difference between said measurements.

28. The apparatus of claim 21, wherein said attribute is amplitude of the signal.

29. The apparatus of claim 28, wherein said signal is characterized by a predetermined set of frequencies, and wherein said amplitude is an amplitude of each frequency in the set of frequencies relative to amplitudes of other frequencies in the frequency set.

30. The apparatus of claim 21, wherein the at least one receiver is further configured to determine the measurements for a plurality of time intervals; and the processor is further configured to calculate the change in signal path length and calculate the volumetric change for the plurality of time intervals.

31. The apparatus of claim 21, wherein said signal is an Ultra-wide Band (UWB) RF signal characterized by a bandwidth which is larger than 500 Mhz.

32. The apparatus of claim 21, wherein said attribute is time-of-arrival of the signal.

33. The apparatus of claim 21, wherein at least one of the at least one transmitter and at least one of the at least one receiver are positioned on the circumference of the chest wall.

34. The apparatus of claim 21, wherein the apparatus comprises a plurality of pairs of transmitters and receivers, said pairs operating with the signal by time division multiple access (TDMA) to avoid signal interference.

35. The apparatus of claim 21, wherein the time interval is a fraction of the breathing cycle.

36. The apparatus of claim 21, wherein at least one of the at least one receiver is connected to a corresponding transmitter by a reference cable that carries a reference signal, a corresponding attribute of the reference signal being indicative of an attribute of a transmitted signal.

37. The apparatus of claim 21, wherein the apparatus is further capable of calculating a tidal volume for the breathing cycle.

38. The apparatus of claim 37, wherein the apparatus is further capable of measuring respiratory rate and generating an alarm if the tidal volume is within a pre-specified range, and the respiratory rate is normal.

39. The apparatus of claim 37, wherein the apparatus is further capable of generating a first indication if the tidal volume is below a first threshold, and a second indication if the tidal volume is above a second threshold, wherein the second threshold is larger than the first threshold and the difference between the first and second threshold is below 10% of normal tidal volume.

40. The apparatus of claim 21, wherein the at least one receiver is configured to determine the measurements for a plurality of time intervals; and the processor is configured to calculate the change in signal path length and calculate the volumetric change for the plurality of time intervals, and wherein the apparatus is further capable of detecting a breathing pattern, from a set of pre-defined breathing patterns, based on volumetric changes during the plurality of time intervals.

41. A non-transitory computer usable medium having a computer readable program code embodied therein, said computer readable program code adapted to be executed to perform a method of monitoring volumetric change of a lung during a breathing cycle by using an electronic signal, including:
receiving by a receiver an electronic signal transmitted from a transmitter, wherein a path of the signal contours at least part of a circumference of a chest wall of the lung;
determining by the receiver measurements of an attribute of the signal received at the beginning and the end of a time interval during the breathing cycle;
calculating by a processor a change in length of signal path during the time interval based on the measurements of the attribute of the signal received at the beginning and the end of the time interval; and
calculating by the processor a volumetric change during the time interval based on the change in signal path length.

42. A wearable device integrating an apparatus capable of monitoring a volumetric change of a lung during a breathing cycle by using an electronic signal, the apparatus comprising at least one transmitter and a receiving module, the receiving module including at least one receiver operatively connected to a processor, wherein:
the at least one transmitter is configured to transmit the electronic signal, wherein a path of the signal contours at least part of a circumference of a chest wall of the lung;
the at least one receiver is configured to:
receive the electronic signal transmitted from the at least one transmitter, and determine measurements of an attribute of the signal received at the beginning and the end of a time interval during the breathing cycle;
the processor is configured to:
calculate a change in length of the signal path during the time interval based on the measurements of the attribute of the signal received at the beginning and the end of the time interval; and
calculate the volumetric change of the lung during the time interval based on the change in signal path length.

43. A wearable device operating in accordance with a method of monitoring volumetric change of a lung during a breathing cycle by using an electronic signal, the method comprising:
receiving by a receiver an electronic signal transmitted from a transmitter, wherein a path of the signal contours at least part of a circumference of a chest wall of the lung;
determining by the receiver measurements of an attribute of the signal received at the beginning and the end of a time interval during the breathing cycle;
calculating by a processor a change in length of the signal path during the time interval based on the measurements of the attribute of the signal received at the beginning and the end of the time interval; and
calculating by the processor a volumetric change during the time interval based on the change in signal path length.

* * * * *